United States Patent
Gejdos et al.

(10) Patent No.: US 7,996,245 B2
(45) Date of Patent: Aug. 9, 2011

(54) PATIENT-CENTRIC HEALTHCARE INFORMATION MAINTENANCE

(75) Inventors: Igor Gejdos, Indianapolis, IN (US); Schuyler Buck, Muncie, IN (US); David Bradley Markisohn, Indianapolis, IN (US); Morris J. Young, Indianapolis, IN (US); Timothy L. Beck, Pendleton, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 744 days.

(21) Appl. No.: 11/999,874

(22) Filed: Dec. 7, 2007

(65) Prior Publication Data
US 2009/0150176 A1 Jun. 11, 2009

(51) Int. Cl.
G06Q 10/00 (2006.01)
G06Q 50/00 (2006.01)
G06G 7/00 (2006.01)
G06F 17/00 (2006.01)

(52) U.S. Cl. .................................. 705/3; 705/2
(58) Field of Classification Search .................. 705/2–3
See application file for complete search history.

(56) References Cited

U.S. PATENT DOCUMENTS

| | | | |
|---|---|---|---|
| 5,251,126 A | 10/1993 | Kahn et al. | |
| 5,497,486 A | 3/1996 | Stolfo et al. | |
| 5,671,404 A | 9/1997 | Lizee et al. | |
| 5,671,409 A | 9/1997 | Fatseas et al. | |
| 5,951,300 A | 9/1999 | Brown | |
| 5,995,962 A | 11/1999 | Horowitz | |
| 6,024,699 A | 2/2000 | Surwit et al. | |
| 6,032,119 A | 2/2000 | Brown et al. | |
| 6,322,502 B1 | 11/2001 | Schoenberg et al. | |
| 6,425,863 B1 | 7/2002 | Werner et al. | |
| 6,562,001 B2 | 5/2003 | Lebel et al. | |
| 6,564,105 B2 | 5/2003 | Starkweather et al. | |

(Continued)

FOREIGN PATENT DOCUMENTS
DE 20217855 2/2003
(Continued)

OTHER PUBLICATIONS

Wang, C. et al.; "*A CORBA-Based Object Framework with Patient Identification Translation and Dynamic Linking, Methods for Exchanging Patient Data*," Methods of Information in Medicine, Mar. 1999, pp. 56-65, vol. 38, No. 1, F.K.Schattauer Verlagsgesellschaft mbH, Germany.

(Continued)

*Primary Examiner* — Gerald J. O'Connor
*Assistant Examiner* — Minnah Seoh
(74) *Attorney, Agent, or Firm* — Baker & Daniels LLP

(57) ABSTRACT

A system for facilitating patient centric healthcare information maintenance. For example, a health management software system may be operated to receive, organize, and use patient medical information. The health management software may comprise a database for storing, retrieving, organizing, displaying, and, generally, for managing a patient's health. In one exemplary embodiment, the health management software system is used in conjunction with a healthcare maintenance device, such as a blood glucose monitoring system. The blood glucose monitoring system may contain several database objects in the form of data records. Typically in a portable blood glucose monitor, each data record contains a time and a concentration data element, or a time-amount point. Similarly, an insulin pump, which is another exemplary embodiment of a healthcare maintenance device, may maintain data records with time and dosage information, or a time-dosage point.

24 Claims, 11 Drawing Sheets

U.S. PATENT DOCUMENTS

| | | |
|---|---|---|
| 6,571,128 B2 | 5/2003 | Lebel et al. |
| 6,577,899 B2 | 6/2003 | Lebel et al. |
| 6,585,644 B2 | 7/2003 | Lebel et al. |
| 6,605,038 B1 | 8/2003 | Teller et al. |
| 6,635,014 B2 | 10/2003 | Starkweather et al. |
| 6,648,821 B2 | 11/2003 | Lebel et al. |
| 6,659,948 B2 | 12/2003 | Lebel et al. |
| 6,668,196 B1 | 12/2003 | Villegas et al. |
| 6,684,191 B1 | 1/2004 | Barnard et al. |
| 6,687,546 B2 | 2/2004 | Lebel et al. |
| 6,694,191 B2 | 2/2004 | Starkweather et al. |
| 6,733,446 B2 | 5/2004 | Lebel et al. |
| 6,740,075 B2 | 5/2004 | Lebel et al. |
| 6,748,402 B1 | 6/2004 | Reeves |
| 6,758,810 B2 | 7/2004 | Lebel et al. |
| 6,781,522 B2 | 8/2004 | Sleva et al. |
| 6,804,656 B1 | 10/2004 | Rosenfeld et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,852,104 B2 | 2/2005 | Blomquist |
| 6,873,268 B2 | 3/2005 | Lebel et al. |
| 6,873,807 B2 | 3/2005 | Umetsu |
| 6,958,705 B2 | 10/2005 | Lebel et al. |
| 6,990,434 B2 | 1/2006 | Minogue et al. |
| 7,020,508 B2 | 3/2006 | Stivoric et al. |
| 7,024,236 B2 | 4/2006 | Ford et al. |
| 7,029,455 B2 | 4/2006 | Flaherty |
| 7,041,468 B2 | 5/2006 | Drucker et al. |
| 7,050,735 B2 | 5/2006 | Bardolatzy et al. |
| 7,063,665 B2 | 6/2006 | Hasegawa et al. |
| 7,082,334 B2 | 7/2006 | Boute et al. |
| 7,113,946 B2 | 9/2006 | Cosic |
| 7,120,488 B2 | 10/2006 | Nova et al. |
| 7,165,062 B2 | 1/2007 | O'Rourke |
| 7,179,226 B2 | 2/2007 | Crothall et al. |
| 7,181,350 B2 | 2/2007 | Oberding et al. |
| 7,207,009 B1 | 4/2007 | Aamodt et al. |
| 2002/0016568 A1 | 2/2002 | Lebel et al. |
| 2002/0029776 A1 | 3/2002 | Blomquist |
| 2002/0040208 A1 | 4/2002 | Flaherty et al. |
| 2002/0059299 A1 | 5/2002 | Spaey |
| 2002/0140976 A1 | 10/2002 | Borg et al. |
| 2002/0193679 A1 | 12/2002 | Malave et al. |
| 2003/0002848 A1 | 1/2003 | Kawaoka et al. |
| 2003/0011646 A1 | 1/2003 | Levine et al. |
| 2003/0065308 A1 | 4/2003 | Lebel et al. |
| 2003/0065536 A1 | 4/2003 | Hansen et al. |
| 2003/0069758 A1 | 4/2003 | Anderson et al. |
| 2003/0098869 A1 | 5/2003 | Arnold et al. |
| 2003/0140044 A1 | 7/2003 | Mok et al. |
| 2003/0145206 A1 | 7/2003 | Wolosewicz et al. |
| 2003/0163088 A1 | 8/2003 | Blomquist |
| 2003/0199739 A1 | 10/2003 | Gordon et al. |
| 2003/0208465 A1 | 11/2003 | Yurko et al. |
| 2004/0030987 A1 | 2/2004 | Manelli |
| 2004/0038389 A1 | 2/2004 | Maus et al. |
| 2004/0073464 A1 | 4/2004 | Huang |
| 2004/0086314 A1 | 5/2004 | Chen et al. |
| 2004/0111296 A1 | 6/2004 | Rosenfeld et al. |
| 2004/0119742 A1 | 6/2004 | Silbey et al. |
| 2004/0172284 A1 | 9/2004 | Sullivan et al. |
| 2005/0004947 A1 | 1/2005 | Emlet et al. |
| 2005/0010452 A1 | 1/2005 | Lusen |
| 2005/0137653 A1 | 6/2005 | Friedman et al. |
| 2005/0159977 A1 | 7/2005 | Green et al. |
| 2005/0182655 A1 | 8/2005 | Merzlak et al. |
| 2005/0187794 A1* | 8/2005 | Kimak ............... 705/3 |
| 2005/0192844 A1 | 9/2005 | Esler et al. |
| 2005/0259945 A1 | 11/2005 | Splaver |
| 2006/0010014 A1 | 1/2006 | Brown |
| 2006/0020491 A1 | 1/2006 | Mongeon et al. |
| 2006/0031094 A1 | 2/2006 | Cohen et al. |
| 2006/0095298 A1 | 5/2006 | Bina |
| 2006/0155581 A1 | 7/2006 | Eisenberger et al. |
| 2006/0161460 A1 | 7/2006 | Smitherman et al. |
| 2006/0167367 A1 | 7/2006 | Stanczak et al. |
| 2006/0178910 A1 | 8/2006 | Eisenberger et al. |
| 2006/0184524 A1 | 8/2006 | Pollanz |
| 2006/0224638 A1 | 10/2006 | Wald et al. |
| 2006/0272652 A1 | 12/2006 | Stocker et al. |
| 2007/0033074 A1 | 2/2007 | Nitzan et al. |
| 2007/0048691 A1 | 3/2007 | Brown |
| 2007/0055940 A1 | 3/2007 | Moore et al. |
| 2007/0088525 A1 | 4/2007 | Fotiades et al. |
| 2007/0089071 A1 | 4/2007 | Zinn et al. |
| 2007/0179352 A1 | 8/2007 | Randlov et al. |
| 2007/0179975 A1 | 8/2007 | Teh et al. |
| 2007/0185390 A1 | 8/2007 | Perkins et al. |
| 2007/0189590 A1 | 8/2007 | Fidrich et al. |
| 2007/0219432 A1 | 9/2007 | Thompson |
| 2007/0232866 A1 | 10/2007 | Nephin et al. |
| 2007/0276197 A1 | 11/2007 | Harmon |

FOREIGN PATENT DOCUMENTS

| | | |
|---|---|---|
| EP | 0970655 | 1/2000 |
| EP | 0649316 | 12/2000 |
| EP | 1194864 | 4/2002 |
| EP | 1416417 | 5/2004 |
| EP | 1647929 | 4/2006 |
| EP | 1662417 | 5/2006 |
| JP | 04/145774 | 5/2004 |
| JP | 04/145775 | 5/2004 |
| JP | 04/145776 | 5/2004 |
| JP | 07/058685 | 3/2007 |
| WO | WO9609590 | 3/1996 |
| WO | WO0018449 | 4/2000 |
| WO | WO0065522 | 11/2000 |
| WO | WO0072181 | 11/2000 |
| WO | WO0174229 | 10/2001 |
| WO | WO0200111 | 1/2002 |
| WO | WO0278512 | 10/2002 |
| WO | WO03015838 | 2/2003 |
| WO | WO2005037095 | 4/2005 |
| WO | WO2005096206 | 10/2005 |
| WO | WO2006050485 | 5/2006 |
| WO | WO2007005530 | 1/2007 |
| WO | WO2007084502 | 7/2007 |
| WO | WO2007093482 | 8/2007 |

OTHER PUBLICATIONS

Bilenko, M. et al.; "*Adaptive Name Matching in Information Integration*," IEEE Intelligent Systems; Sep. 2003, vol. 18, No. 5; p. 16-23, IEEE Computer Society.

Frenger, Paul; "*GRANNIE 2: a Ubiguitious, Protean Robotic Guardian Angel*," Automation Science and Engineering, Sep. 1, 2007, pp. 857-862, IEEE International Conference on IEEE.

Frenger, Paul; "*GRANNIE: A Scalable, Interactive, Artificial Intelligence Supervisory System for Medical Devices*," Proceedings of Can. Med. Bio. Engr. Conference, 2007, p. 256-259.

"CoPilot Health Management System Version 3.1," User's Guide, Mar. 2007, 230 pp., ART 10641 Rev. D, Abbott Diabetes Care, Inc.

"MediSense® Precision Link® Diabetes Data Management Software," User's Guide, May 2006, 58 pp., 116-412 Rev. AC, Abbott Diabetes Care, Inc.

Albisser, Michael A.; "A Graphical User Interface for Diabetes Management Than Integrates Glucose Prediction and Decision Support," Diabetes Technology & Therapeutics, 2005, pp. 264-273, vol. 7, No. 2.

Janssen et al., "Acensia® Winglucofacts® Professional Intelligent Diabetes Management Software Is An Effective Tool for the Management of Diabetes," Bayer HealthCare Clinical Summary Report, Jul. 2005, 10 pp.

Joshy et al.; "Diabetes Information Systems: A Rapidly Emerging Support for Diabetes Surveillance and Care," Diabetes Technology & Therapeutics, 2006, pp. 587-597, vol. 8, No. 5.

"OneTouch Diabetes Management Software," User Manual, 2006, 173 pp. v. 2.3.1, Lifescan, Inc.

"Getting Started, CareLink Personal Therapy Management Software for Diabetes," Brochure, 2007, 20 pp., Medtronic Minimed, Inc.

"Accu-Chek® Camit Pro Diabetes Management Software," User's Manual, 2005, 220 pp., v.2.1 and Addendum v. 2.4, Roche Diagnostics Corp.

"Accu-Chek® Compass Diabetes Care Software," User's Guide, 2005, 74 pp., Roche Diagnostics Corp.

"Accu-Chek® Diabetes Assistant," accessed with notional data and printed from www.diabetesassistant.com on Jan. 16, 2007, 20 pp., Roche Diagnostics Corp.

PCT International Search Report and Written Opinion of the International Search Authority for Pat. Appl. No. PCT/EP2008/009857.

* cited by examiner

| | Date and Time | Information | Error |
|---|---|---|---|
| | 4/26/2006 9:04 am | bG: 85 mg/dL | |
| ⊗ | | bG: 105 mg/dL | Missing date and time |
| | 4/25/2006 11:54 pm | bG: 94 mg/dL | |
| | 4/25/2006 9:10 am | bG: 115 mg/dL | |
| ⚠ | 4/16/2006 1:26 pm | bG: 80 mg/dL | Out of sequence |
| | 4/16/2006 5:15 pm | bG: 75 mg/dL | |

DELETE   ACCEPT AS IS   REASSIGN   DEVICE REASSIGN

PRINT   OK   CANCEL

PATIENT-CENTRIC HEALTHCARE INFORMATION MAINTENANCE

FIELD OF THE INVENTION

The present invention relates to patient centric healthcare information maintenance.

BACKGROUND OF THE INVENTION

Many fields of medical treatment and healthcare require monitoring of certain body functions. Thus, e.g., for patients suffering from diabetes, a regular check of the blood glucose level forms an essential part of the daily routine. The blood glucose level has to be determined quickly and reliably several times per day. Health monitoring devices are used to facilitate the collection of medical information without unduly disturbing the lifestyle of the patient. A large number of health monitoring devices for monitoring various body functions are commercially available.

Nevertheless, the use of health monitoring devices involves some risks which are mainly due to the complexity of using health monitoring devices. The risks are sometimes more pronounced for elderly patients or infants. Misuse of the health monitoring devices may lead to handling failures and to insufficient or even inaccurate information. Further, since many of the patients handling the health monitoring devices have not undergone medical training, the interpretation of the medical data collected by the health monitoring devices may be challenging to them. Often, patients are required to see their doctors in short time-intervals on a regular basis.

To reduce the frequency of necessary visits to doctors, the idea of home care gained popularity over the recent years. The availability of communication networks, such as the internet and wireless communication networks, led to the development of health management systems that enable transmission of patient medical data from the patient's home to a healthcare center by using health monitoring devices and data transfer systems. U.S. Pat. No. 7,103,578 and U.S. Published Application No. 2004/0172284 disclose two such methods and systems, the disclosures of which are incorporated by reference.

Known health management systems have several disadvantages. Some systems provide limited interaction capabilities to patients and care givers. Often, systems have limited analytical capabilities. Further, many health management systems do not permit collection of additional data or modification of data collected by the health management system. A need remains for systems that facilitate the use and interpretation of patient medical data.

SUMMARY OF THE INVENTION

The present invention relates to patient centric healthcare information maintenance. For example, a health management software system may be operated to receive, organize, and use patient medical information. The health management software may comprise a database for storing, retrieving, organizing, displaying, and, generally, for managing a patient's health. In one exemplary embodiment, the health management software system is used in conjunction with a healthcare maintenance (HCM) device, such as a blood glucose monitoring system. The blood glucose monitoring system may contain several database objects in the form of data records. Typically in a portable blood glucose monitor, each data record contains a time and a concentration data element, or a time-amount point. Similarly, an insulin pump, which is another exemplary embodiment of a healthcare maintenance device, may maintain data records with time and dosage information, or a time-dosage point.

To analyze the data in a HCM device, the data may be copied or transferred to a computer, typically by loading into a database. When data is transferred from an HCM device to a computer, the HCM device often includes self-identifying information along with the patient data. The computer may then create device data tables that associate the self-identifying information of each HCM device to a particular patient. In one exemplary embodiment, the HCM device may include a specific patient identifier with the time-amount data. While the computer may assume that there is a direct correspondence between the HCM device, the patient, and the time-amount data, the HCM device itself may be used by different people and may be used inappropriately such that incorrect readings are made.

Therefore, each data record that is transferred from a HCM device is tagged by the health management software system as a new entry. Once the transfer is complete, the user may select an undo option. When the undo option is selected by the user, each of the transferred entries, each representing a particular time-amount data point, may be selected by the user for deletion or re-assignment. For example, if the user notices that one of the data points has an invalid value (e.g., a missed reading by a glucose monitor) then that particular invalid value may be deleted by the user. In one embodiment, such a deleted data record is erased from the database. In another embodiment, such a deleted data record is marked as deleted and identification of the person making the deletion is stored—allowing a subsequent reviewer to see all the deleted records and decide if the deletion was proper. Additionally, in another exemplary embodiment, the user may reassign a particular data point to another patient. Further, in one exemplary embodiment, the user may also reassign the HCM device to another patient, so that all the transferred data would be associated with a new patient and all future data from that particular HCM device would be associated with the selected new patient.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein.

Figure 1:
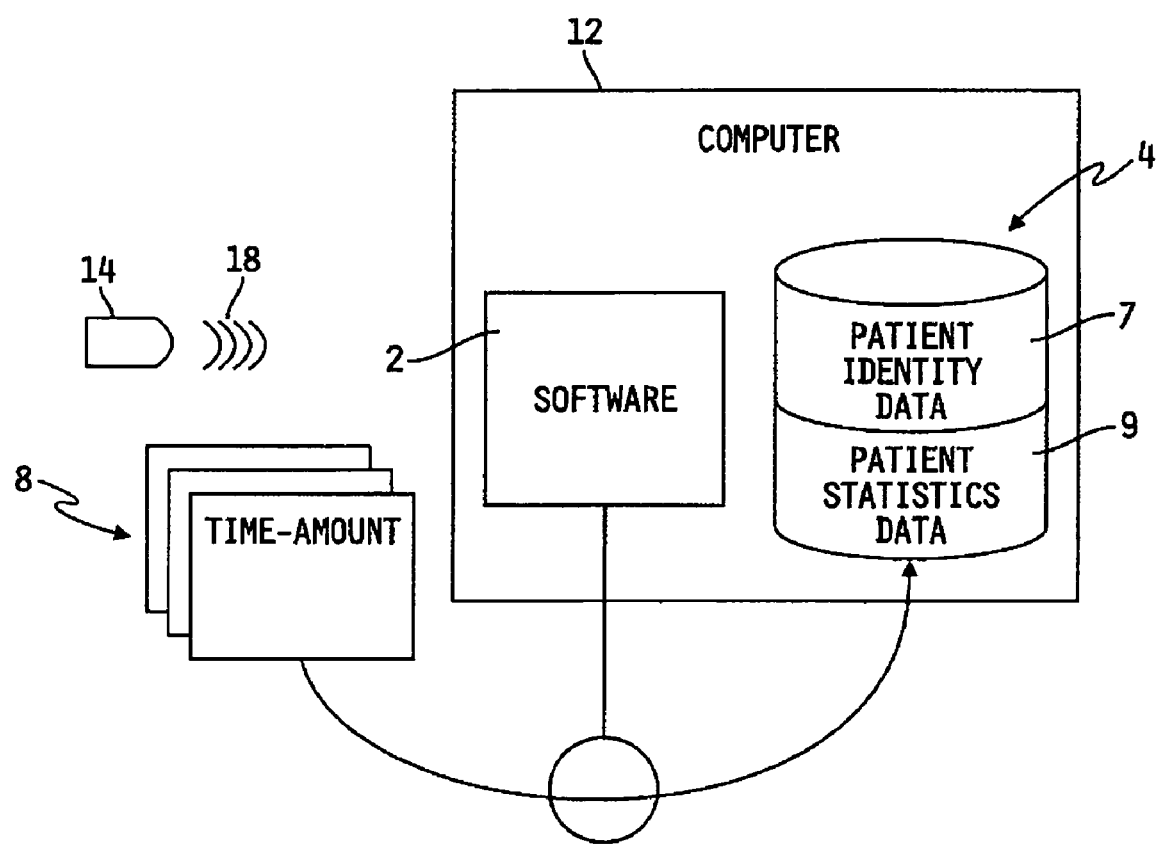
FIG. 1 is a schematic operation diagram of the software and database systems according to an exemplary embodiment of the present invention.

Corresponding reference characters indicate corresponding parts throughout the several views. Although the drawings represent embodiments of various features and components according to the present invention, the drawings are not necessarily to scale and certain features may be exaggerated in order to better illustrate and explain the present invention. The exemplifications set out herein illustrate preferred embodiments of the invention and such exemplifications are not to be construed as limiting the scope of the invention in any manner.

DETAILED DESCRIPTION OF EMBODIMENTS OF THE INVENTION

For the purposes of promoting an understanding of the principles of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrated devices and described methods and further applications of the principles of the invention which would normally occur to one skilled in the art to which the invention relates.

The detailed descriptions which follow are presented in part in terms of algorithms and symbolic representations of operations on data bits within a computer memory representing alphanumeric characters or other information. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared, and otherwise manipulated. It proves convenient at times, principally for reasons of common usage, to refer to these signals as bits, values, symbols, characters, display data, terms, numbers, or the like. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements which impart a physical organization on the information stored in memory. More than mere abstraction, the data structures are specific electrical or magnetic structural elements in memory which simultaneously represent complex data accurately and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein which form part of the present invention; the operations are machine operations. Useful machines for performing the operations of the present invention include general purpose digital computers or other similar devices. In all cases the distinction between the method operations in operating a computer and the method of computation itself should be recognized. The present invention relates to a method and apparatus for operating a computer in processing electrical or other (e.g., mechanical, chemical) physical signals to generate other desired physical signals.

The present invention also relates to an apparatus for performing these operations. This apparatus may be specifically constructed for the required purposes or it may comprise a general purpose computer as selectively activated or reconfigured by a computer program stored in the computer. The algorithms presented herein are not inherently related to any particular computer or other apparatus. In particular, various general purpose machines may be used with programs written in accordance with the teachings herein, or it may prove more convenient to construct more specialized apparatus to perform the required method steps. The required structure for a variety of these machines will appear from the description below.

The present invention deals with "object-oriented" software, and particularly with an "object-oriented" operating system. The "object-oriented" software is organized into "objects," each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects.

Both programs and databases may be objects. In the case of databases, the data portion of the object may be significantly larger than the methods portion, The actual physical implementation of a database on a general purpose computer may take several forms, from complete individual records storing the substantive information with several key indexes for locating a particular record, to a plurality of tables interrelated by relational operations, to a matrix of cross-linked data records, to various combinations and hybrids of these general types. In particular physical devices, a database may be structured and arranged to accommodate the restrictions of the physical device—but when transferred to a general purpose computer be able to be stored in a variety of formats. Thus, while certain types of information may be described as being stored in a "database" from a conceptual standpoint, generally such information may be electronically stored in a variety of structures with a variety of encoding techniques.

Databases may contain many types of information, and may store the information in a variety of encoding techniques. When a database stores information that relates to a particular person, product, location, or other thing, the database typically uses a unique identifier that binds the "concept" of the person, product, location, or other thing with a storable piece of data. When the unique identifier is used to reference the data record, the unique identifier is termed a "key" and data records associated with the "concept" are said to be "keyed" by the unique identifier. The association between a key and its data may be implemented in a variety of ways, for example by having the key be a field in a corresponding data record, by having a key value in a search tree with an associated pointer to one or more data records corresponding to the key, or by encoding the corresponding information with a value that upon decoding produces the unique identifier and the corresponding data, etc. By these various methods, instances of data may be associated with, or "bound" with or to, the "concept" by using the key.

The terms "network," "local area network," "LAN," "wide area network," or "WAN" mean two or more computers which are connected in such a manner that messages may be transmitted between the computers. In such computer networks, typically one or more computers operate as a "server," a computer with large storage devices such as hard disk drives and communication hardware to operate peripheral devices such as printers or modems. Other computers, termed "workstations," provide a user interface so that users of computer networks can access the network resources, such as shared data files, common peripheral devices, and inter-workstation communication. The computers have at least one processor for executing machine instructions, and memory for storing instructions and other information. Many combinations of processing circuitry and information storing equipment are known by those of ordinary skill in these arts. A processor may be a microprocessor, a digital signal processor ("DSP"), a central processing unit ("CPU"), or other circuit or equivalent capable of interpreting instructions or performing logical actions on information. Memory includes both volatile and non-volatile memory, including temporary and cache, in electronic, magnetic, optical, printed, or other format used to store information. Users activate computer programs or network resources to create "processes" which include both the general operation of the computer program along with specific operating characteristics determined by input variables and its environment.

Concepts described below may be further explained in one of more of the co-filed patent applications entitled HELP UTILITY FUNCTIONALITY AND ARCHITECTURE; U.S. patent application Ser. No. 11/999,906, METHOD AND SYSTEM FOR GRAPHICALLY INDICATING MULTIPLE DATA VALUES; U.S. patent application Ser. No. 11/999,853, SYSTEM AND METHOD FOR DATABASE INTEGRITY CHECKING; U.S. patent application Ser. No. 11/999,856, METHOD AND SYSTEM FOR DATA SOURCE AND MODIFICATION TRACKING; U.S. patent application Ser. No. 11/999,888, EXPORT FILE FORMAT WITH MANIFEST FOR ENHANCED DATA TRANSFER; U.S. patent application Ser. No. 11/999,867, GRAPHIC ZOOM FUNCTIONALITY FOR A CUSTOM REPORT; U.S. patent application Ser. No. 11/999,932, METHOD AND SYSTEM FOR SELECTIVE MERGING OF PATIENT DATA; U.S. patent application Ser. No. 11/999,859, METHOD AND SYSTEM FOR PERSONAL MEDICAL DATA DATABASE MERGING; U.S. patent application Ser. No. 11/999,772, METHOD AND SYSTEM FOR WIRELESS DEVICE COMMUNICATION; U.S. patent application Ser. No. 11/999,879, METHOD AND SYSTEM FOR SETTING TIME BLOCKS; U.S. patent application Ser. No. 11/999,968, METHOD AND SYSTEM FOR ENHANCED DATA TRANSFER; U.S. patent application Ser. No. 11/999,911, COMMON EXTENSIBLE DATA EXCHANGE FORMAT; U.S. patent application Ser. No. 11/999,871, METHOD OF CLONING SERVER INSTALLATION TO A NETWORK CLIENT; U.S. patent application Ser. No. 11/999,876, METHOD AND SYSTEM FOR QUERYING A DATABASE; U.S. patent application Ser. No. 11/999,912, METHOD AND SYSTEM FOR EVENT BASED DATA COMPARISON; U.S. patent application Ser. No. 11/999,921, DYNAMIC COMMUNICATION STACK; U.S. patent application Ser. No. 11/999,934, SYSTEM AND METHOD FOR REPORTING MEDICAL INFORMATION; U.S. patent application Ser. No. 11/999,878, METHOD AND SYSTEM FOR MERGING EXTENSIBLE DATA INTO A DATABASE USING GLOBALLY UNIQUE IDENTIFIERS; U.S. patent application Ser. No. 11/999,947, METHOD AND SYSTEM FOR ACTIVATING FEATURES AND FUNCTIONS OF A CONSOLIDATED SOFTWARE APPLICATION; U.S. patent application Ser. No. 11/999,880, METHOD AND SYSTEM FOR CONFIGURING A CONSOLIDATED SOFTWARE APPLICATION; U.S. patent application Ser. No. 11/999,894, METHOD AND SYSTEM FOR DATA SELECTION AND DISPLAY; U.S. patent application Ser. No. 11/999,896, METHOD AND SYSTEM FOR ASSOCIATING DATABASE CONTENT FOR SECURITY ENHANCEMENT; U.S. patent application Ser. No. 11/999,951, METHOD AND SYSTEM FOR CREATING REPORTS; U.S. patent application Ser. No. 11/999,851, METHOD AND SYSTEM FOR CREATING USER-DEFINED OUTPUTS; U.S. patent application Ser. No. 11/999,905, DATA DRIVEN COMMUNICATION PROTOCOL GRAMMAR; U.S. patent application Ser. No. 11/999,770, HEALTHCARE MANAGEMENT SYSTEM HAVING IMPROVED PRINTING OF DISPLAY SCREEN INFORMATION; (U.S. patent application Ser. No. 11/999,855), and METHOD AND SYSTEM FOR MULTI-DEVICE COMMUNICATION; U.S. patent application Ser. No. 11/999,866, the entire disclosures of which are hereby expressly incorporated herein by reference. It should be understood that the concepts described below may relate to diabetes management software systems for tracking and analyzing health data, such as, for example, the Accu-Chek® 360° product provided by Roche Diagnostics. However, the concepts described herein may also have applicability to apparatuses, methods, systems, and software in fields that are unrelated to healthcare. Furthermore, it should be understood that references in this patent application to devices, meters, monitors, pumps, or related terms are intended to encompass any currently existing or later developed apparatus that includes some or all of the features attributed to the referred to apparatus, including but not limited to the Accu-Chek® Active, Accu-Chek® Aviva, Accu-Chek® Compact, Accu-Chek® Compact Plus, Accu-Chek® Integra, Accu-Chek® Go, Accu-Chek® Performa, Accu-Chek® Spirit, Accu-Chek® D-Tron Plus, and Accu-Chek® Voicemate Plus, all provided by Roche Diagnostics or divisions thereof.

The present invention relates to patient centric healthcare information maintenance. For example, the present invention may include health management software system 2, an embodiment of which is shown in FIG. 1, which comprises one or more programs configured to receive, organize, and use patient medical information. The health management software comprises database 4 for storing, retrieving, organizing, displaying, and, generally, for managing a patient's health. In this context, the term "patient" refers to a person whose medical information is stored in the health management software. Patient medical information comprises administrative data and medical data. Patient administrative data comprises non-medical data related to the identification of patients ("patient identity data") and administration of patients and patient records ("patient non-identity data"). Patient identity data includes name, address, phone number, etc. Patient non-identity data includes information pertaining to insurance providers etc. Patient medical data, or medical data, means qualitative and quantitative data relating to a patient state such as, for example, test results, laboratory values, measurements, observations, treatment or dosage values, prescriptions. In addition to blood glucose values mentioned herein, exemplary medical data may include A1c values, Albumin values, Albumin excretion values, body mass index values, blood pressure values, carbohydrate values, cholesterol values (total, HDL, LDL, ratio) creatinine values, fructosamine values, HbA1 values, height values, insulin dose values, insulin rate values, total daily insulin values, ketone values, microalbumin values, proteinuria values, heart rate values, temperature values, triglyceride values, and weight values. Medical data may be provided by the patient, a healthcare professional, a healthcare devise, a caregiver, or anyone having relevant data pertaining to a patient. While the invention is described herein with reference to medical devices, and more particularly, with reference to diabetes management devices, the invention is applicable to any download data obtained from any device.

For example, in blood glucose monitoring system 6, several database objects may be useful in organizing the data. Typically in a portable monitor, such as HCM device 14, each data record contains a time and a concentration data element, or a time-amount point. Similarly, an insulin pump maintains data records with time and dosage information, or a time-dosage point. The information in the monitor or pump may have a particular structure, or may be serially stored with each item of information being implicit with its location. While the monitor or pump (collectively, "health care management device" or "HCM device") may have further information, relating to the patient or other aspects of the blood, the time and amount are the typical data points used by a physician to evaluate the patient ("time-amount data"). The foregoing description of embodiments of the invention relate to the combination of time and amount data, other embodiments are contemplated by the present invention that include time independent data, non-numerical data, and other combinations of types of data. The computer system of the patient or doctor typically has both stored data and associated programs that analyze the stored data. To analyze the data in the HCM device, the data may be copied or transferred to the computer, typically by loading into a database.

In one embodiment, the user of HCM device 14 may start the process of downloading data from HCM device 14 with a download utility of glucose monitoring system 6. The process begins when the download utility accesses HCM device 14, and it ends when the utility stops downloading device records. During a download, one or more device records are downloaded from HCM device 14. Re-launching the download utility creates a new download event. In one embodiment, the user waits while the download utility receives data from HCM device 14. In another embodiment, the user may continue to use the glucose monitoring system 6 management software while the download utility receives data from HCM device 14 in the background.

When data 8 is transferred from HCM device 14 to computer 12, HCM device 14 includes self-identifying information along with the patient data. Although the software is described herein for operation on a computer (e.g., desktop, laptop or tablet), it should be understood that the principles of the invention may be embodied in software for operation on various devices, including but not limited to personal digital assistants ("PDAs"), infusion pumps, blood glucose meters, cellular phones, or integrated devices including a glucose measurement engine and a PDA or cellular device. Transferred data 8 may be formatted as data fields, or may be raw data. Typically, transferred data 8 does not include any patient identifying information. Rather, computer 12 has device data tables that associate the self-identifying information of each HCM device to a particular patient. Thus, computer 12 uses HCM device 14 self-identifying information to infer the patient with whom the time-amount data should be associated. Alternatively, HCM device 14 may include a specific patient identifier with the time-amount data. Typically, HCM device's self-identifying information is a key to all the data associated with the corresponding HCM device 14. In addition, the HCM device key is associated with a patient identifier or patient key. However, while computer 12 may assume that there is a direct correspondence between HCM device 14, patient, and the time-amount data, HCM device 14 itself may be used by different people and may be used inappropriately such that incorrect readings are made.

With the association between the time-amount data determined, computer 12 may then create or supplement patient statistics database 9 with the set or plurality of time-amount points imported from HCM device 14 which constitutes the download data records. Initially, patient statistics database 9 may be independent of any other data, although generally such patient statistics data is desired to be combined with previously obtained patient statistics data to provide a database covering several collections of time-amount points. Typically, each patient would have her own database 4 spanning the use of HCM device 14 by that patient, and possibly data from other HCM devices, or other medical or personal data.

In addition to the plurality of time-amount data assembled and compiled from HCM device 14, computer database 4 may also include other information about a patient. This other data may include information relating to the time-amount data or may simply relate to the characteristics of the patient. It is also possible that computer 12 may store other measured readings relating to the patient (for example, heart rate or red blood cell count) that might be useful to a physician in diagnosing the patient. Such additional patient data may be stored as a separate database, may be integrated into a patient data record, or may be commingled with the time-amount data as in a combined graph.

Figures 2, 3:
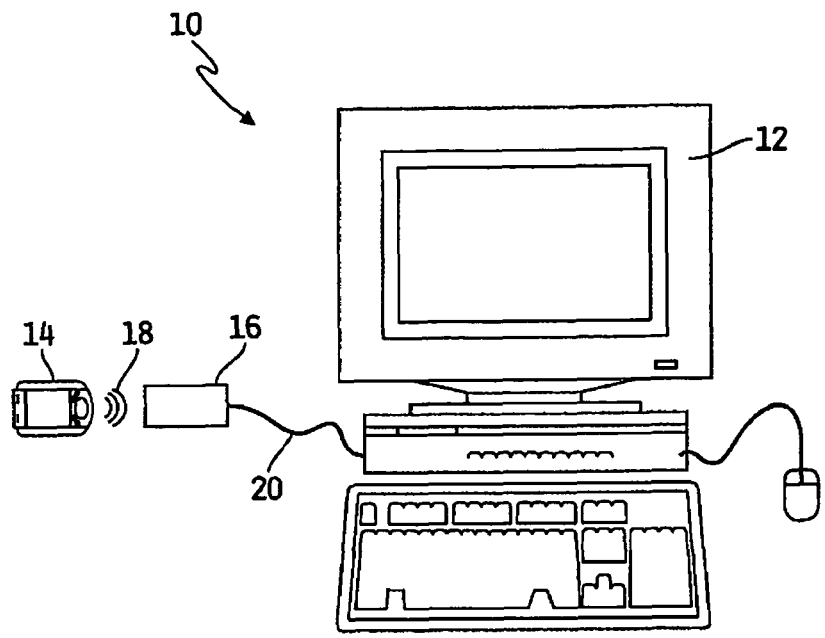
FIG. 2 is a schematic view of a health care management system.
FIG. 3 is a screenshot of an undo operation according to an exemplary embodiment of the present invention.

Referring to FIG. 2, system 10 may also comprise HCM device 14 capable of electronic communication with computer 12 and configured to provide medical data to health management software 2 (FIG. 1). In the embodiment shown, data collection cable 20 connects computer 12 to data collector 16. HCM device 14 is capable of electronic communication with the data collector 16. In the exemplary embodiment, health management device communicates medical data by means of infrared signal 18 to data collector 16. In another embodiment (not shown), HCM device 14 has a direct connection to a USB port (not shown) of computer 12 and transmits medical data through a wired connection. In a still further embodiment (not shown), HCM device 14 transmits medical data over a WiFi transmission to data collector 16, which in this embodiment is a WiFi receiver. HCM devices are devices capable of recording information and transferring the information to health management software 2. HCM device 14 may comprise a HCM device which records values of measurements relating to a patient's state (e.g., blood glucose level) and information such as the time and date when the measurement was recorded. HCM device 14 may also comprise a device configured to provide medications to patients such as, for example, insulin pumps. A medication providing device, generally, records dosage amounts as well as the time and date when medication is provided. Optionally, HCM device 14 may have an input device, such as a keyboard, to enable a user to provide additional manually entered data. HCM device 14 may also comprise a computer, a PDA, or a phone.

Each HCM device 14 is, generally, assigned to a patient and associated with that patient in health management software 2. Thus, when medical data from HCM device 14 is transferred to health management software 2, the medical data from HCM device 14 automatically populates database records relating to that patient. Typically, the association between the patient and a particular HCM device 14 is maintained by each HCM device 14 having a unique identifier (e.g., an external patient identifier) that is bound to the patient. Each download of medical data from HCM device 14 thus creates a new set of distinct download data records which is processed by system 10.

System 10 may be used by the patient, a healthcare professional, a caregiver, or anyone having relevant data pertaining to a patient. System 10 may be located in a patient's home, a healthcare facility, or any other convenient place. In an alternative embodiment, two systems may be connected and medical data may be transferred between them. For example, a first system may be located in a place accessible to the patient or a caregiver, and a second system may be located in a healthcare facility. In this embodiment, the first and second systems are configured to transfer medical data between them by any means known in the art such as, for example, via the Internet, cellular communications, or the physical transfer of a memory devise such as a diskette, USB key, or compact disc. The first system, or patient system, may be configured to receive medical data from a health management device and the second system may be configured to also receive medical data from a health management device or, alternatively, to receive medical data transferred from the first system. The second system, or healthcare system, may be configured to receive medical data from a plurality of patient systems.

The health management software is configured to show and store medical data in a plurality of forms and formats. Medical data may be shown on a video display or a printed report in record, graphic, or tabular format. The first step for the software user is to obtain medical data from the medical device, such as an insulin pump or glucose monitor. Typically, the user collects medical data from HCM device 14 periodically, and computer 12 maintains a database of the accumulated medical data. Often, such medical data includes information covering both the dosages (e.g., when HCM device 14 is an insulin pump) and the patient measurements (e.g., when HCM device 14 is a glucose monitor).

As medical information is transferred from HCM device 14, each device data record is included as a new entry in the download data records. In the event that a user desires to remove download data records transferred from HCM device 14, an "UNDO" option may be used. When the UNDO option is selected by the user, the download data records, which are distinct from the other data records of the databases of computer 12, may be selected by the user for deletion. Optionally, the download data records may be individually selected by the user for deletion or re-assignment. For example, if the user notices that one of the data points has an invalid value (e.g., a missed reading by a glucose monitor) then that particular invalid value may be deleted by the user. In one embodiment, such a deleted data record is erased from the database. In another embodiment, such a deleted data record is marked as deleted and identification of the person making the deletion is stored—allowing a subsequent reviewer to see all the deleted records and decide if the deletion was proper. Another option is to reassign a particular data point (e.g., when a glucose monitor has been used on a different person) to another patient (typically done at the second computer at a physician's office, but could be done at a patient's home computer if more than one patient use the computer to track health care values). A third option involves reassigning HCM device 14 to another patient, so that the download data records would be associated with a new patient and all future data from that particular HCM device 14 would be associated with the selected new patient.

As shown in FIG. 3, if the "UNDO" button or menu item is selected by a user an exemplary Undo screen appears. In the screen, the plurality of download data records most recently loaded from HCM device 14 is displayed with a check box or other selection tool adjacent to the download data records, or alternatively a check box or other selection tools is provided for each record. In one embodiment, the menu of options is listed on the screen. With this display, the user may select the records desired and the particular operation desired, ranging from deleting all the selected records, to ignoring the selected records, accept the selected records, reassign the selected records to another user, or reassign HCM device 14 to another user.

The tracking of new data records may be maintained by health management software system 2 in a log file, so that as long as the log file information persists, multiple undo operations are possible. When a user desires to reassign the data to another patient, both the data merge functionality and the duplicate patient functionality, described in detail below, may be used to select an appropriate patient to merge the health care maintenance information.

Figure 4:
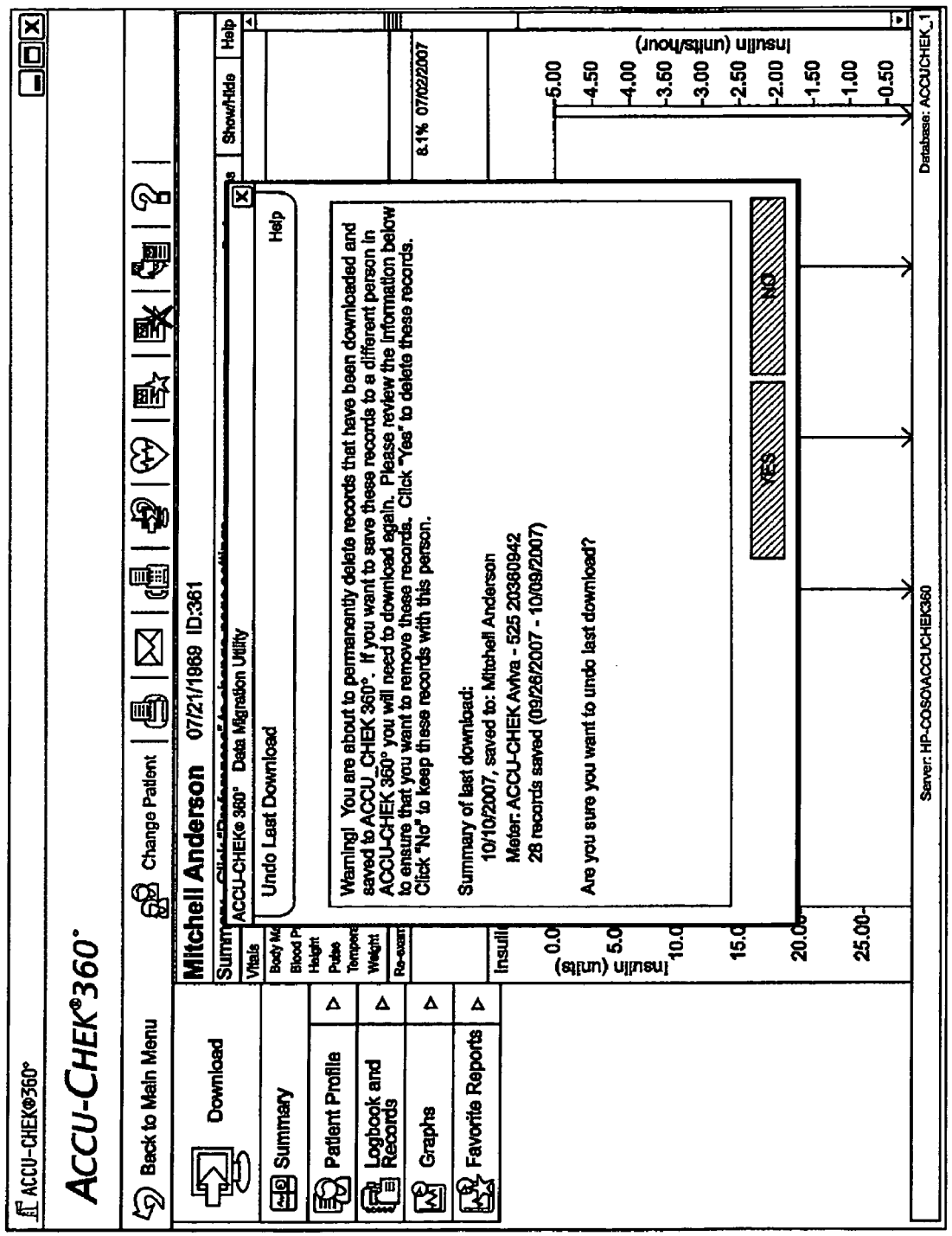
FIG. 4 is a screenshot of an undo operation according to another exemplary embodiment of the present invention.

In another exemplary embodiment, shown in FIG. 4, by selecting the "UNDO" button or menu item, another exemplary undo screen is displayed that allows the user to undo, i.e., remove, all records from the last download of HCM device 14 from database 4 (FIG. 1). As shown in FIG. 4, this page displays a warning to the user and a summary of the last download, including the date, patient, device information, number of records downloaded, and the date range for the records downloaded. The user is then asked to indicate that they are sure they want to undo the last download. If yes is selected, the records from the last download of HCM device 14 are removed from database 4. The download "UNDO" function may be implemented with other download procedures, including the download procedures disclosed in copending U.S. patent application entitled METHOD AND SYSTEM FOR ENHANCED DATA TRANSFER, the disclosure of which is incorporated by reference.

Health management software 2 may also include a data comparison program that is utilized to identify medical information stored in a first location, i.e., a source database, that is unique to, a duplicate of, and/or a potential duplicate of medical information stored in a second location, i.e., a destination database. Computer 12 may be running health management software 2, i.e., medical management software, such as diabetes management software, and encrypt and save the medical information transferred from HCM device 14 in one of a source format database or a destination format database. The information received from HCM device 14 will be encrypted according to an encryption feature that is specific to HCM device 14. Thus, if another HCM device is used to upload information to computer 12, it will be encrypted according to the specific encryption feature of that device. As set forth above, HCM device 14 may also assign to the patient an external system identification that may be used to correlate the patient to a particular HCM device. As the medical information is being uploaded to computer 12 or other storage media connected thereto, the data comparison utility may be used to identify medical information stored in on HCM device 14 that is unique thereto, a duplicate of, and/or a potential duplicate of medical information stored on computer 12 or other storage media connected thereto using the same or a substantially similar process as described in detail below with specific reference to a data migration utility.

The data comparison program may be in the form of a machine-readable program that is adapted to be utilized independent of or as an integral component of medical management software, such as diabetes management software. For example, the data comparison program may be formed as an object within the medical management software or, alternatively, may be stand alone software capable of independent operation and installation. In one exemplary embodiment, the data comparison program may be activated from the medical management software after the medical management software has been launched to compare a source database with a destination database. In another exemplary embodiment, the data comparison program may be utilized in conjunction with and/or formed as a component of a data migration utility. The data migration utility may also be in the form of a machine-readable program that is adapted to be utilized independent of or as an integral component of medical management software, such as diabetes management software. The operation of the data migration utility is set forth below and includes a detailed description of the operation of the data comparison program in the context of the data migration utility. While described in detail herein with specific reference to the data migration utility, the data comparison program may be used as a stand alone component and/or at different points during a data transfer process and nothing contained herein should be viewed as limiting the scope of the invention to this exemplary embodiment.

Figure 5A:
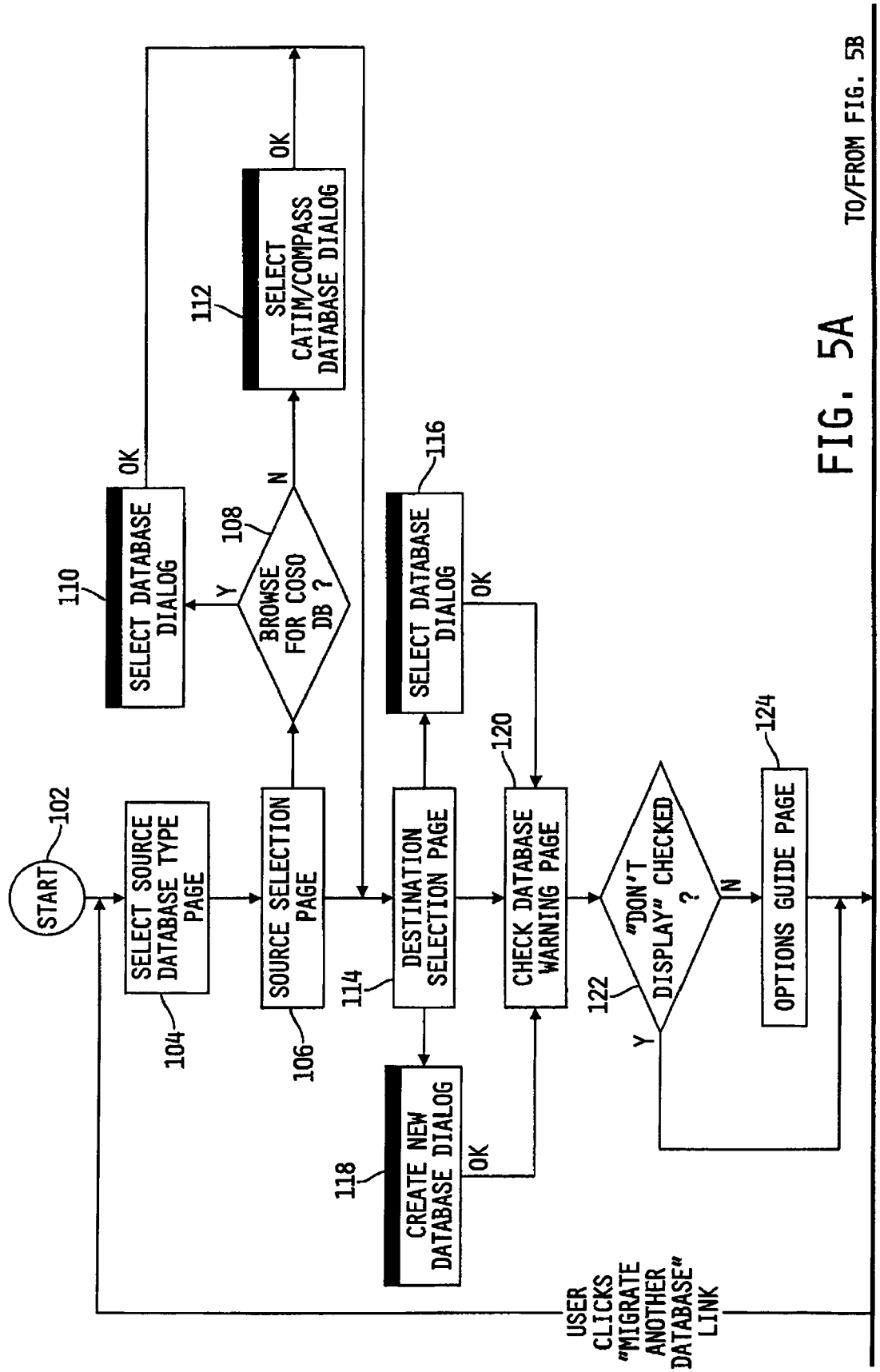
FIG. 5A and FIG. 5B are is a flowchart diagram views of a data migration process using the methodology of an exemplary embodiment of the present invention.

The data migration utility is utilized to migrate medical information in a source database to a destination database that may also contain medical information. Referring to FIG. 5A, the data migration utility is launched at Start 102 on flowchart 100. In one exemplary embodiment, once the data migration utility is launched, a user may be prompted for information by dynamic questionnaires in a wizard format. For example, the user may be prompted to set the rules governing the migration of data. Referring to Step 104, the user may be prompted to select a source database stored in a source format for migration into a destination database stored in destination format at the source database type page shown in FIG. 6. The source database type page allows the user to select a database type from a list of various database types meeting the necessary requirements for migration into the destination database. For example, the database types listed may include only those databases that will be compatible with the medical management software once merged into destination database and converted from source format into destination format.

Figure 6:
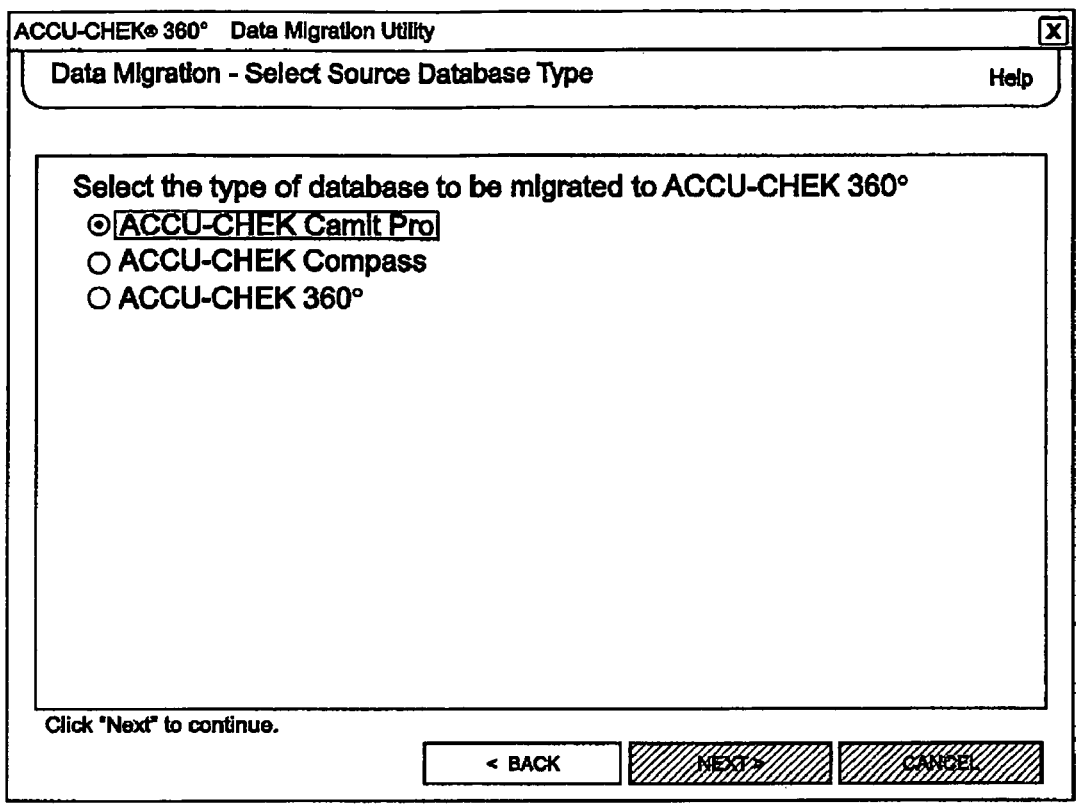
FIG. 6 is a screenshot of a source database type page according to an exemplary embodiment of the present invention.

In one exemplary embodiment, the medical management software is diabetes management software. Referring to FIG. 6, a list of databases that are compatible with the diabetes management software once merged into a destination database is provided. Specifically, as shown in FIG. 6, the source databases include, but are not limited to, databases associated with a glucose monitoring device or glucose monitoring software, such as those associated with ACCU-CHEK® Camit Pro, ACCU-CHEK® Compass, and ACCU-CHEK® 360°.

As shown in FIG. 6, positioned adjacent to each source database type displayed on the source database type page is a corresponding button. In one exemplary embodiment, only a single button may be selected at any given time. However, in other exemplary embodiments, multiple buttons may be selected for multiple, simultaneous database migration. By selecting the button corresponding to the desired source database type, a next or finish button may appear on the source database type page. By selecting the next or finish button, the user may progress to the next questionnaire in the data migration utility.

Figure 7:
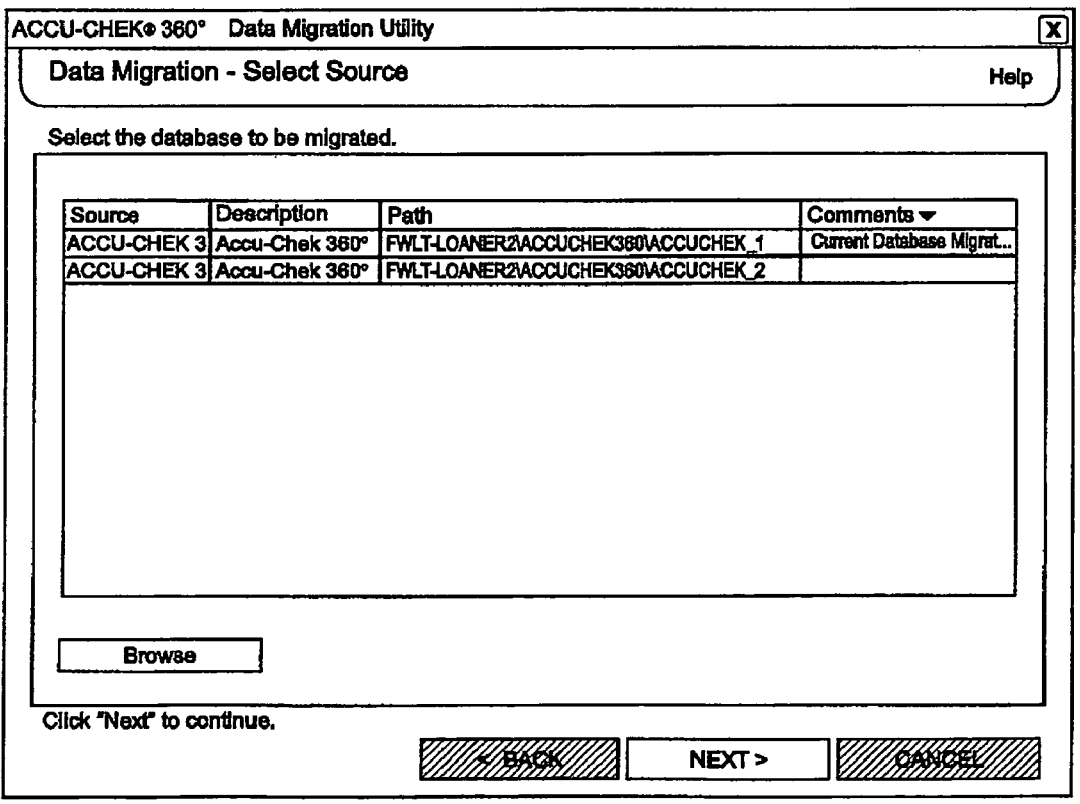
FIG. 7 is a screenshot of a source database selection page according to an exemplary embodiment of the present invention.

Once a source database type is selected and the user has also selected the next or finish button, the data migration utility displays a source database selection page at Step 106 in FIG. 5A. Referring to FIG. 7, an exemplary source database selection page is shown that provides a listing of potential source databases by type and that may include general descriptions of the database, the file path for the database, and any comments relevant to the particular database. The source databases may be databases that contain medical information stored in a source format. For example, potential source databases may contain patient medical information that may further include numerous records associated with the individual patient having data fields for patient identity, including title, first name, middle name, last name, suffix, and date of birth, day and week information for the administration of medicine and/or for test results, such as blocks of time and days of week, targeted event information, contact information, such as address, phone number, and email address, emergency contact information, such as name, relation, address, and phone number, demographic information, such as diabetes diet, the diagnosis date, gender, and ethnicity, and diabetes therapy, such as controlled by and date and insulin type information, system identification, i.e., the patient's unique medical management system identification, external system identification, insurance, and healthcare provider data. Similarly, the databases may include healthcare provider information that may further include numerous records associated with healthcare providers having data fields such as healthcare provider title, first name, middle name, and last name, suffix, specialty, practice area, and contact information, such as address, phone number and email address, for example.

The source database selection page may also include a browse button, shown in FIG. 7, which allows a user to manually search the computer's hard drive or other attached media devices for a database location that is not listed on the source database selection page. Referring to Step 108 in FIG. 5A, if the user selects the browse function at the source database selection page by selecting the browse button, Step 110 is executed and the user is prompted to select a file path for the source database. In contrast, if the user does not select the browse feature at Step 108, the user must then select one of the databases identified on the source selection page in step 106.

Irrespective of the method utilized to select the source database, once the source database is selected the data migration utility may then display a destination database selection page at Step 114. The destination database selection page may provide a listing of the potential destination databases stored in a destination format. In one exemplary embodiment, the potential destination databases are databases that are currently used by the medical management software. In one exemplary embodiment, the destination selection page may include a listing of the type of database, a description of each database, the file path for each database, and any comment related to each database. Additionally, the destination database may contain medical information, such as patient medical and/or healthcare provider information, and may include fields identical to or substantially identical to those set forth above with respect to the source database.

Figure 8:
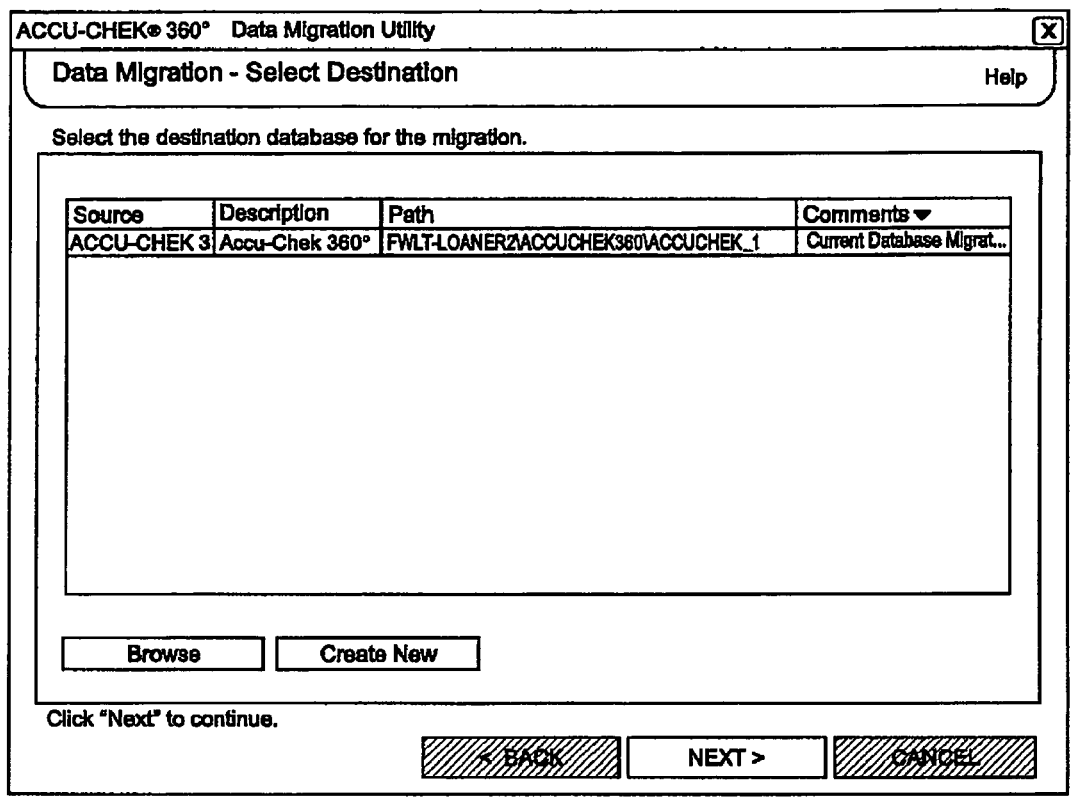
FIG. 8 is a screenshot of a destination database selection page according to an exemplary embodiment of the present invention.

Referring to FIG. 8, which depicts an exemplary destination database selection page, the destination database selection page may include a browse button and/or create new button. If the browse button is selected, the user is directed to select a destination database in the same manner as in step 110 for selecting the source database. If the browse function is not selected, the user may either select one of the databases set forth on the destination database selection page by the data migration utility at Step 116 or, alternatively, the user may select the create new button. If the create new button is selected, a create new destination database dialog is activated at Step 118 and a new destination database is created. In one exemplary embodiment, the data migration utility further prompts the user to determine the file path where the new destination database is to be created. Additionally, the data migration utility may automatically assign the new destination database a file path that is associated with the corresponding medical management software.

Figure 9:
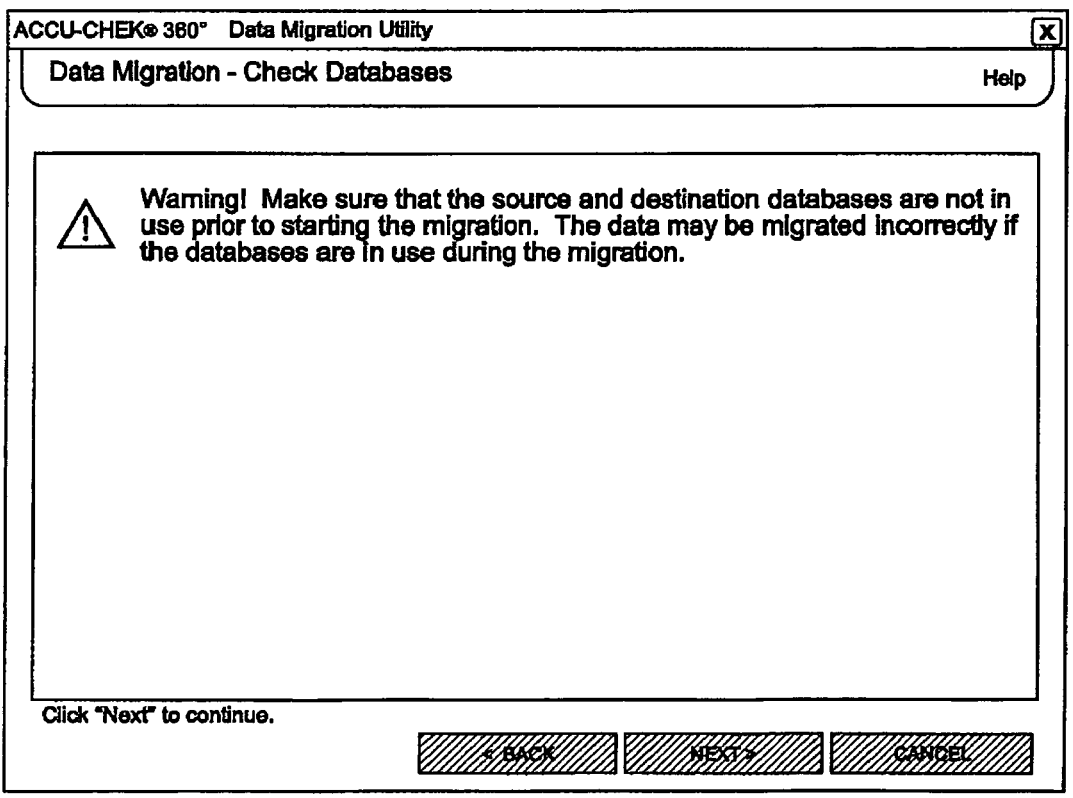
FIG. 9 is a screenshot of a check database warning page according to an exemplary embodiment of the present invention.

Irrespective of the method utilized to select the destination database or whether a new destination database is created, a check database warning page is displayed at Step 120. An exemplary check database warning page is depicted in FIG. 9 and includes a warning to ensure that the source and destination databases are not in use prior to the start of data migration. In another exemplary embodiment, the check database warning page opened at Step 120 in FIG. 5A may further include a next or finish button that requires an affirmative action by the user before the data migration utility may initiate the migration of data from the source database to the destination database and, if necessary, conversion of the same from the source format to the destination format.

Figure 10:
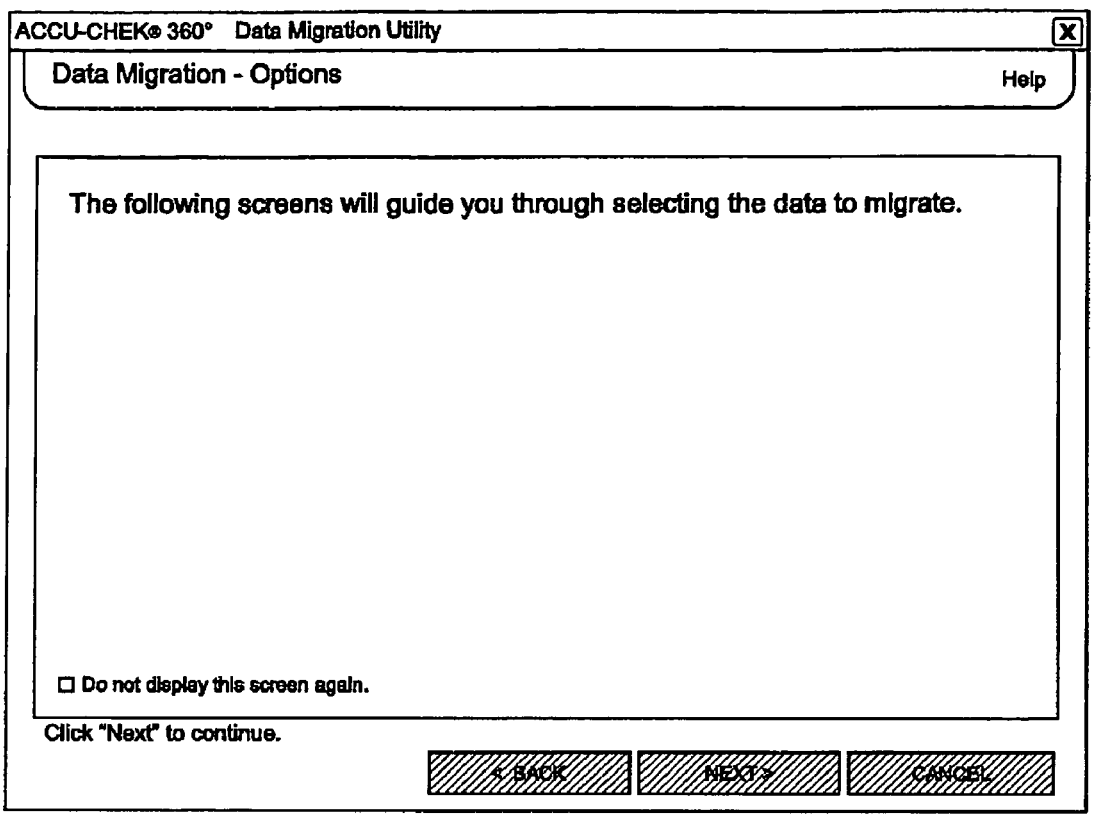
FIG. 10 is a screenshot of an options guide page according to an exemplary embodiment of the present invention.

Once the next or finish button is selected, the data migration utility may open, at Step 124 in FIG. 5A, an options guide page, shown in FIG. 10, to begin the options selection process. The options guide page may include a brief overview of the options guide page process and may also include a "don't display this page again" option with a corresponding button. If the button has previously been selected, then the data migration utility skips opening the options guide page at Step 124. However, if the "don't display this page again" feature has not been previously selected, the options guide page is displayed at Step 124.

Figure 5B:
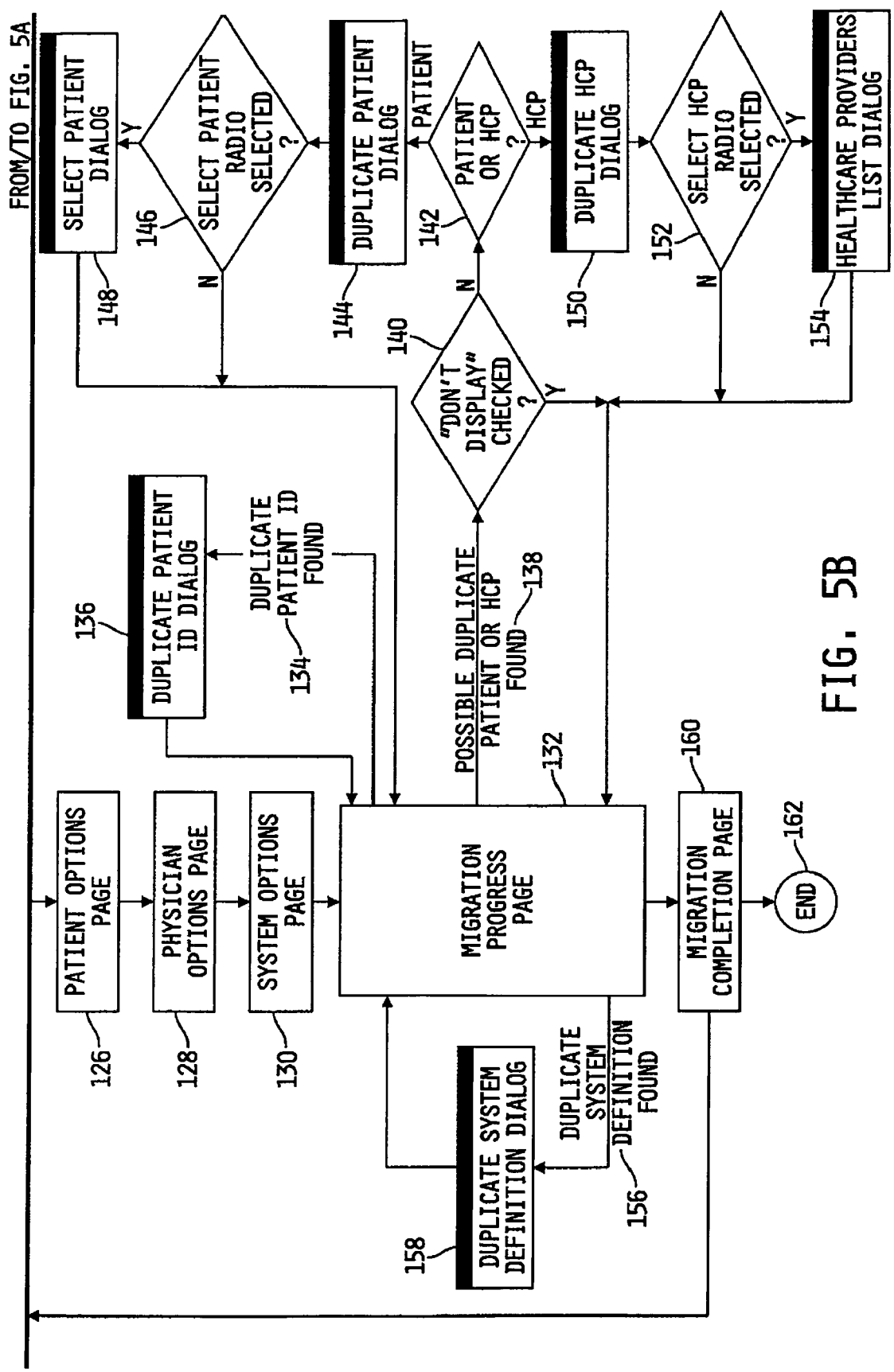
Figure 11:
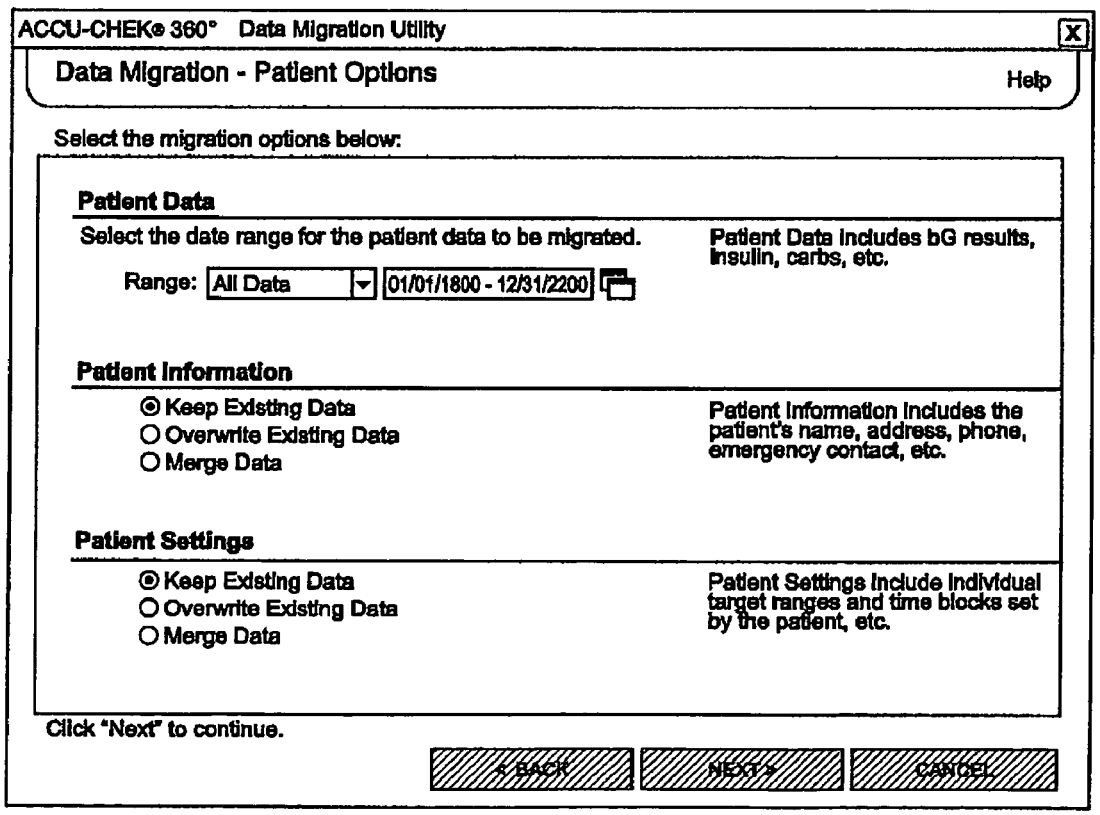
FIG. 11 is a screenshot of a patient options page according to an exemplary embodiment of the present invention.

After displaying the options guide page, a patient options page will be opened at Step 126 in FIG. 5B that will allow the user to select the specific patient related options to be applied during data migration. For example, in one exemplary embodiment, shown in FIG. 11, the patient options page allows for the selection of the date ranges of individual patient records to be migrated into the patient's corresponding file in the destination database. The patient options page may further allow the user to select how individual patient information will be migrated into the destination database. For example, the patient options page may provide buttons to allow the user to select whether patient information from the destination database should be kept, whether patient information from the source database should override patient information in the destination database, or whether patient information in the source database should be merged with patient information in the destination database. Further, the user may also be provided with the option to determine whether individual patient settings in the destination database that may apply to features in the corresponding medical management software should be kept, should be overridden by the individual patient options set in the source database, or should be merged with the individual patient options from the source database.

Figure 12:
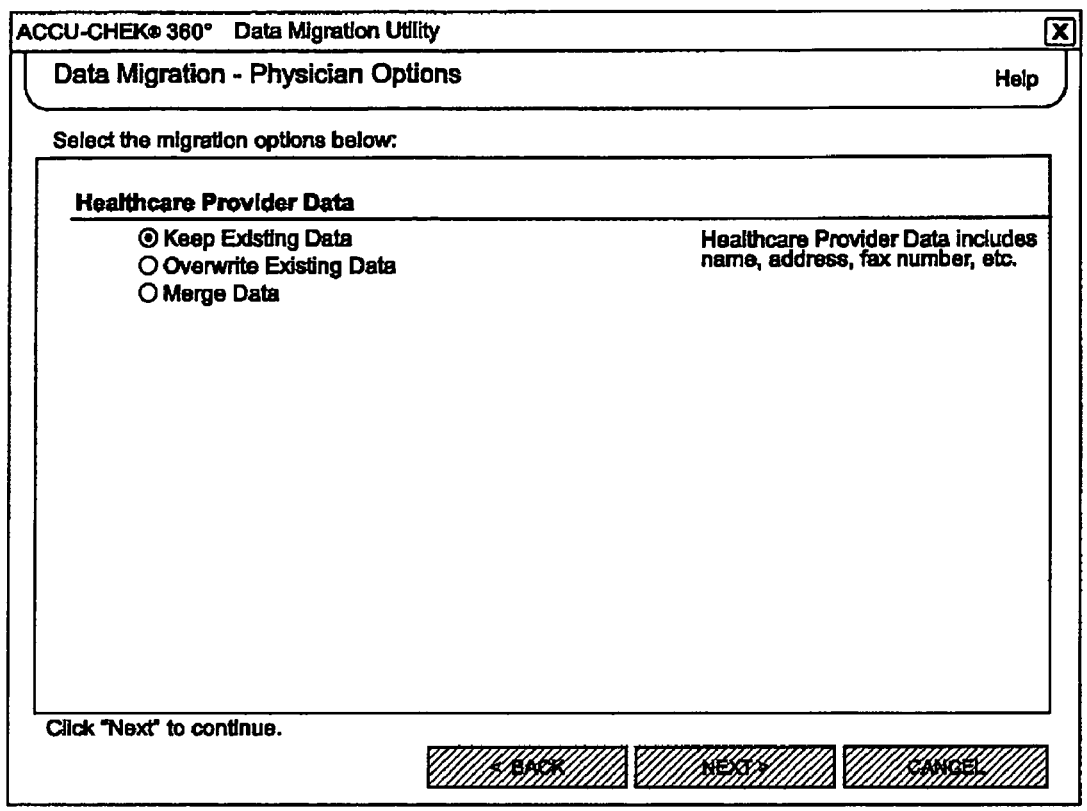
FIG. 12 is a screenshot of a physician options page according to an exemplary embodiment of the present invention.

Once the user has selected the desired patient options at the patient options page, a next button may be provided that the user may select, which results in the opening of a physician options page at Step 128. Referring to FIG. 12, the physician options page may provide a series of buttons for determining whether physician information from the destination database should be kept, whether physician information from the source database should override information in the destination database, or whether physician information in the source database should be merged with the physician information in the destination database. Additionally, in one exemplary embodiment, the user is provided with additional options for determining how physician information is handled during data migration.

Once the user has selected the desired physician options at the physician options page, a next button may be provided that the user may select, which results in the opening of a systems options page at Step 130 in FIG. 5B. The systems option page may allow the user to select various system options, such as options that relate to the medical management software, that should be applied during data migration. Once the system options have been set at Step 130, a next or finish button may be provided that the user may select to close the systems option page and end the options selection process. While the options selection process has been described and depicted herein as a specific series of screens and options, it is contemplated that any of the options and/or screens described herein may be removed and/or additional screens and/or options may be added.

Figure 13:
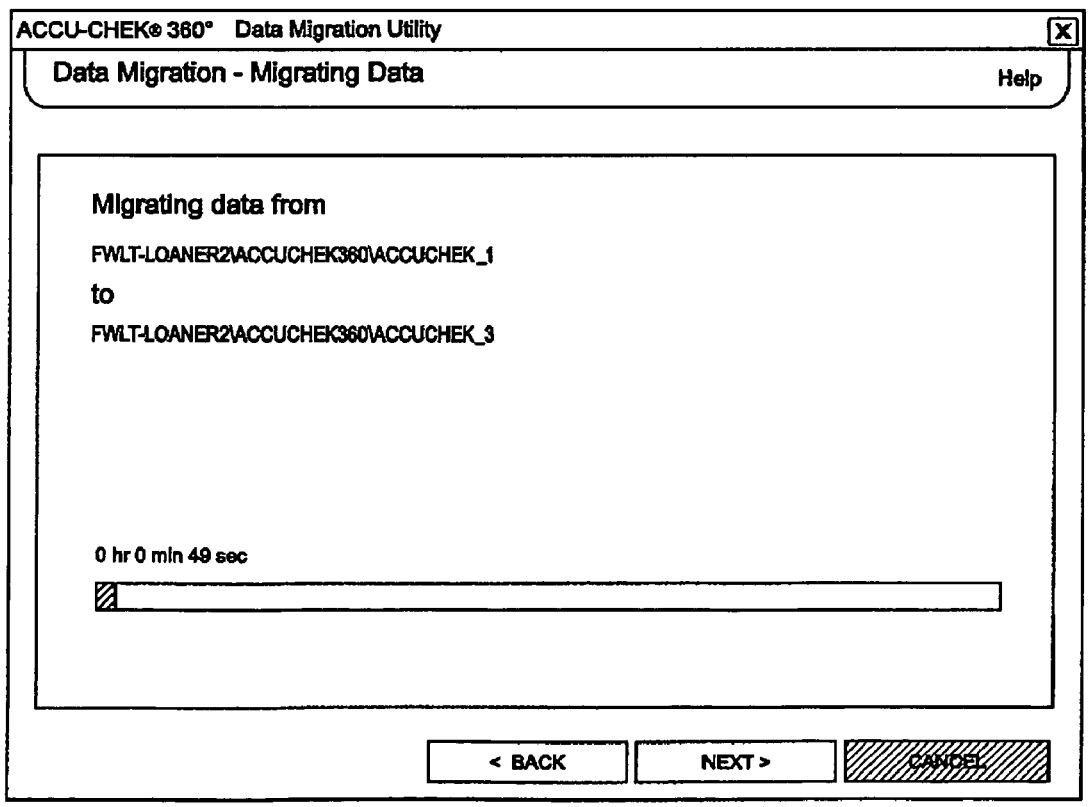
FIG. 13 is a screenshot of a data migration process page according to an exemplary embodiment of the present invention.

Once the options selection process has been completed, the data migration process page, shown in FIG. 13, will open and data migration will begin at Step 132 in FIG. 5B. The data migration process page may show the identity of the source database by the file path and/or by the filename associated with the source database. Similarly, the data migration process page may also show the identity of the destination database by the file path and/or by the filename associated with the destination database. Additionally, the data migration process page may further provide a status bar that depicts in a graphical format the total amount of data to be migrated as compared to the total amount of data that has been migrated. Further, the data migration process page may provide the total amount of time that the data migration utility estimates the data migration to take and/or the amount of time the data migration utility estimates is remaining until data migration is complete.

Once migration has been initiated at Step 132, the data migration utility will begin importing records from the source database and creating corresponding records in the destination database in accordance with the options selected by the user during the options selection process, as set forth in detail above. Specifically, as set forth above, each record may be encrypted according to an encryption method specific to the individual HCM device from which the information was originally uploaded. Thus, the data migration utility may decrypt the medical information associated with a first HCM device that corresponds to an individual patient in the source database and then substantially simultaneously migrate and encrypt the same information into the destination database using the destination database encryption method. This process may then be repeated for subsequent HCM devices corresponding to the same patient or different patients.

Alternatively, the data migration utility may be configured to decrypt medical information contained in the destination database, if any exists, and add it to a temporary database created by the data migration utility. The data migration utility may also decrypt the medical information contained in the source database and merge it into the medical information migrated into the temporary database from the destination database. Once all the medical information from the source database and the destination database has been merged into the temporary database, the information is re-encrypted using the destination database encryption method and saved in the destination database.

Additionally, during data migration, the data migration utility identifies specific medical information, such as medical information corresponding to an individual patient or healthcare provider, and searches the destination database to determine if duplicative or potentially duplicative, i.e., identical or substantially identical, medical information exists in the destination database. In order to determine if duplicative or substantially duplicative medical information exists in the destination database, the data migration utility may utilize the data comparison program. Specifically, as set forth above, the data comparison program may identify at least three categories of patient medical information: unique, duplicate, and potentially duplicate. Alternatively, the data comparison program may provide a numerical rating of the degree of similarity (e.g., 1.0 is a carbon copy, 0.9 is potentially duplicate, 0.8 is highly correlative, etc.). In order to determine the proper classification for each piece of medical information, such as an individual medical record associated with a specific patient, the data comparison program compares the fields associated with the medical information in the source database to the corresponding fields associated with similar medical information in the destination database.

In order to determine if patient medical information in the source database is unique, a duplicate of, or potentially duplicate of patient medical information in the destination database, the data comparison program compares fields for first name, middle name, last name, suffix, date of birth, and unique medical management system identification. Specifically, the data comparison program compares the patient medical information from the source database for an individual patient against the patient medical information from the destination database for a first individual patient. The data comparison program then repeats the comparison of the source database information against a second individual patient in the destination database. This process is repeated until the source database information is compared to the medical information for every individual patient in the destination database. Alternatively, the data comparison program may first start by comparing a key field of the record from the source database with an index of the destination database and only engage in further comparisons if a sufficiently close match is found in the key index of the second database.

In order for the data comparison program to determine that the medical information for an individual patient in the source database is unique as compared to medical information in the destination database, the medical information for the individual patient in the source database must meet any of the following three requirements. First, information in the last name field for the individual patient in the source database must be different from the information in the last name field for every individual patient in the destination database. Second, the information in the date of birth field for the individual patient in the source database must be different from the information in the date of birth field for every individual patient in the destination database. Third, the information in the medical management system identification field for the individual patient in the source database must be both non-null and different from the information in the last name field of every individual patient in the destination database. If any of these three requirements are met, the medical information for the individual patient in the source database is considered unique as compared to the medical information in the destination database and the medical information for the individual patient in the source database is migrated into the destination database and added as a new patient.

Alternatively, if the medical information for the individual patient in the source database is not determined to be unique, the medical information for the individual patient in the source database may be determined to be a duplicate of medical information for the same individual patient that is already in the destination database. In order for the data comparison program to determine that the medical information for an individual patient in the source database is a duplicate of medical information in the destination database, the medical information for the individual patient in the source database must meet one of two conditions. Under the first condition, the medical information is a duplicate if the information in the fields for first name, middle name, last name, suffix, date of birth, and medical management system identification for the individual patient in the source database matches the information in the corresponding fields of the destination database. Alternatively, the information is a duplicate under the second condition if the information in the fields for first name, last name, date of birth, and external identification matches the information in the corresponding fields in the destination database. If either of these conditions are met, the medical information is determined to be duplicative and the patient identified as a duplicate in the data migration utility, as set forth in detail below. However, if the data comparison utility fails to determine that the individual patient's medical information is either unique or duplicative, the medical information is treated as a potential duplicate by the data migration utility.

Similarly, in order to determine if healthcare provider information in the source database is unique, a duplicate of, or a potential duplicate of healthcare provider information in the destination database, the data comparison program compares fields for title, first name, middle name, last name, and suffix. Specifically, the data comparison program compares the healthcare provider information from the source database for an individual healthcare provider against the healthcare provider information from the destination database for a first healthcare provider. The data comparison program then repeats the comparison of the source database information against a second healthcare provider in the destination database. This process is repeated until the source database information is compared to the healthcare provider information for every individual healthcare provider in the destination database.

In order for the data comparison program to determine that the healthcare provider information for an individual healthcare provider in the source database is unique as compared to healthcare provider information in the destination database, the healthcare provider information for the individual healthcare provider in the source database must have information in the last name field that is different from the information in the last name field for every individual healthcare provider in the destination database. If this requirement is met, the healthcare provider information for the individual healthcare provider in the source database is migrated into the destination database and added as a new healthcare provider.

Alternatively, if the healthcare provider information for an individual healthcare provider in the source database is not determined to be unique, the healthcare provider information for the individual healthcare provider in the source database may be determined to be a duplicate of healthcare provider information that is already in the destination database. In order for the data comparison program to determine that the healthcare provider information for an individual healthcare provider in the source database is a duplicate of healthcare provider information in the destination database, the healthcare provider information in the source database must have information in the fields for title, first name, middle name, last name, and suffix that matches the information in the corresponding fields of the destination database. If these conditions are met, the healthcare provider information is determined to be duplicative and the healthcare provider is identified as a duplicate in the data migration utility, as set forth in detail below. However, if the data comparison utility fails to determine that the healthcare provider information is either unique or duplicative, the medical information is treated as a potential duplicate by the data migration utility.

Referring to Step 138 of FIG. 5B, if a duplicative, i.e., identical, patient or healthcare provider is identified, the data migration utility pauses migration and determines at Step 140 if the user has previously indicated that all duplicate patients or healthcare providers should be added as new patients or healthcare providers in the destination database. If the answer is yes, migration resumes and a new patient or healthcare provider is created in the destination database. If the answer is no, the data migration utility determines at Step 142 if the potentially duplicate information corresponds to a patient or a healthcare provider.

Figure 14:
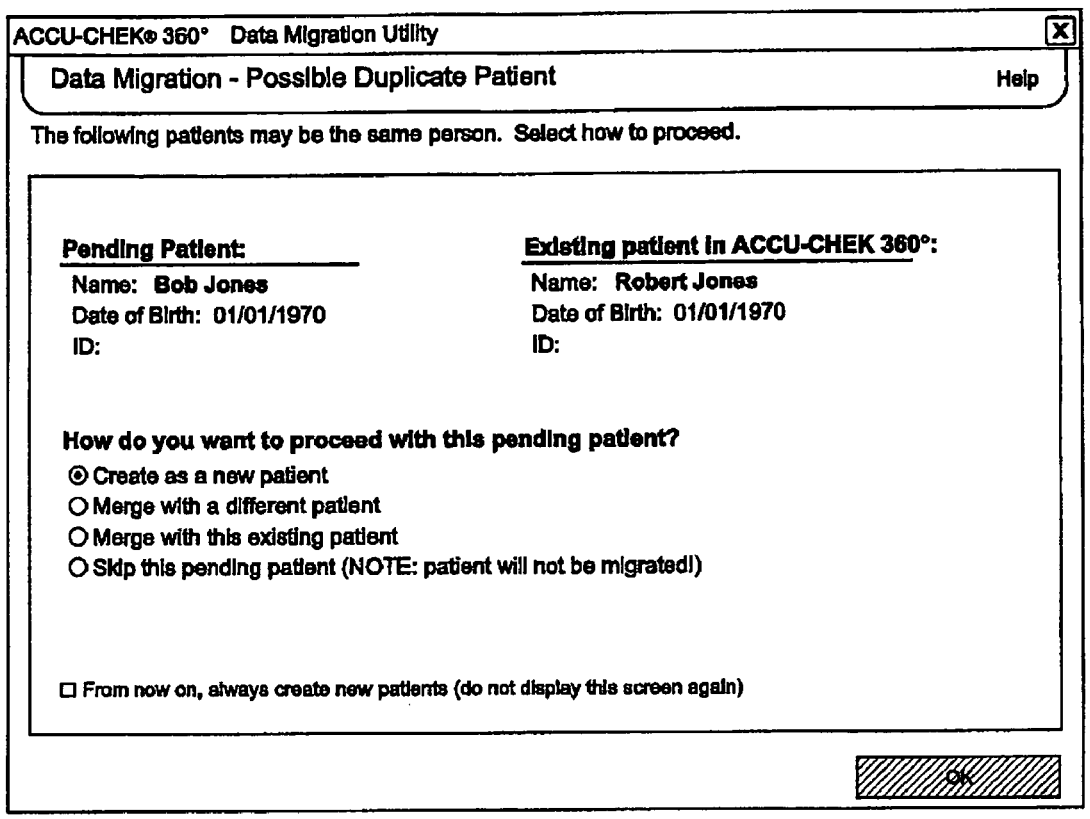
FIG. 14 is a screenshot of a duplicate patient identification dialog according to an exemplary embodiment of the present invention.

If the information corresponds to a patient, a duplicate patient dialog is opened at Step 144. Referring to FIG. 14, the duplicate patient identification dialog may provide information about the pending patient, i.e., the patient in the source database, such as name, date of birth, and the patient's unique medical management system identification. Similarly, the duplicate patient identification dialog may also provide information about the existing patient, i.e., the patient in the destination database, such as name, date of birth, and the patient's unique medical management system identification. The duplicate patient information dialog may then prompt the user to select the manner in which the record in the source database should be treated. For example, the user may select from adding the pending patient as a new patient in the destination database, selecting another patient from the destination database to merge the pending patient's information with, merging the pending patient with the existing patient, or skipping the pending patient, i.e., leaving the pending patient's information in the source database and not adding the same to the destination database.

Once the user has made the desired selection, the user may select an authorization button, such as the OK button in FIG. 14. Once the authorization button is selected, data migration is resumed. However, if at Step 144, the user indicates that another existing patient in the destination database should be merged with the patient in the source database, then, at Step 148, a select patient dialog is opened that allows the user to select a patient from the destination database into which the pending patient data from the source database is merged.

Figure 15:
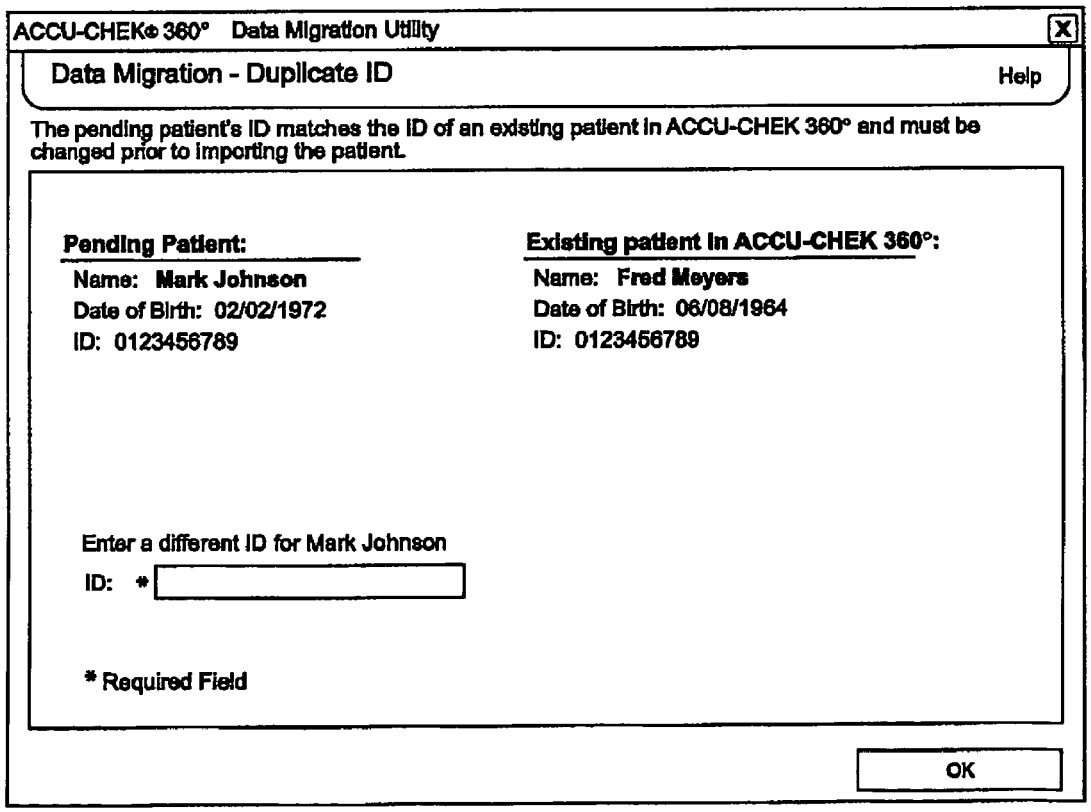
FIG. 15 is a screenshot of a new medical management system identification prompt according to an exemplary embodiment of the present invention.

In one exemplary embodiment, the duplicate patient identification dialog may also include a button that allows the user to avoid the duplicate patient identification dialog for each duplicate patient identified. By selecting this option, each duplicate patient identified by the data migration utility is added as a new patient in the destination database. However, in the event that a pending patient in the source database that is to be added as a new patient in the destination database is determined, at Step 134 in FIG. 5B, to have the same medical management system identification as an existing patient in the destination database, a duplicate identification dialog is opened at Step 136 and data migration paused. As shown in FIG. 15, the duplicate identification dialog prompts the user to enter a new medical management system identification for the pending patient before the patient is added as a new patient in the destination database. Once a new patient identification is entered and an authorization provided by the user, such as by selecting the OK button in FIG. 15, data migration resumes and the pending patient in the source database is added as a new patient in the destination database.

Figure 16:
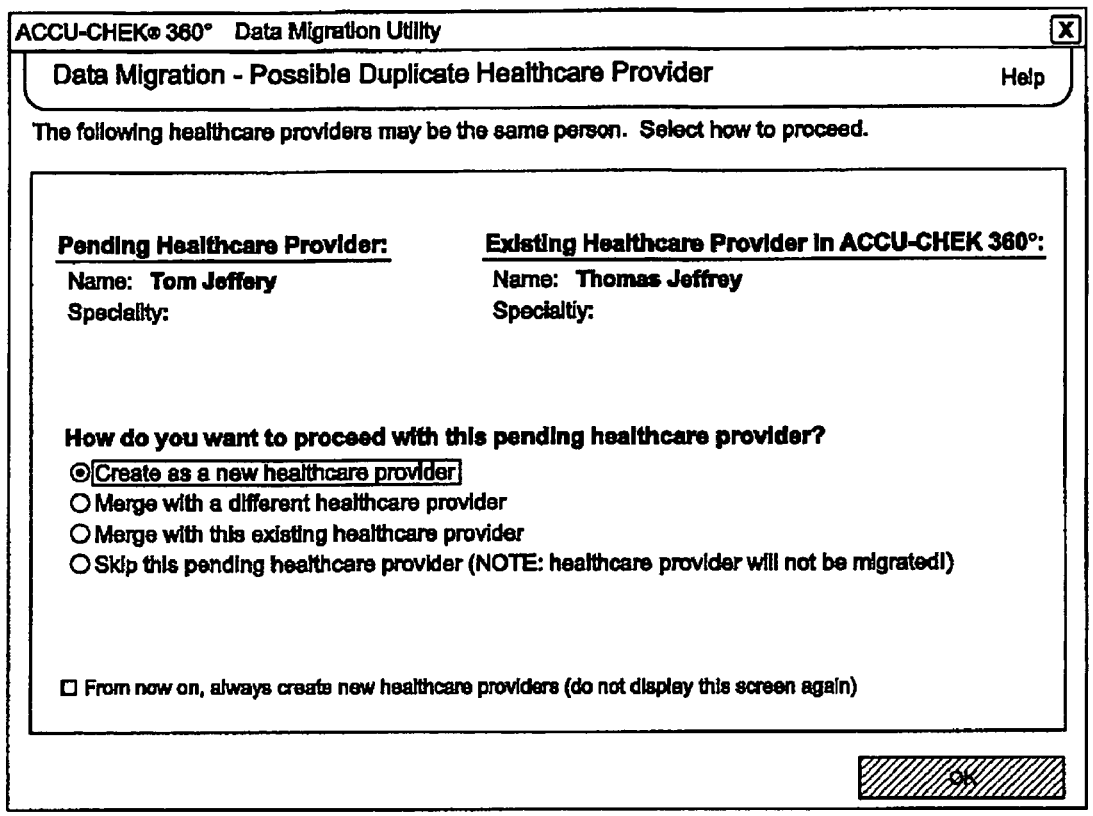
FIG. 16 is a screenshot of a duplicate healthcare provider dialog according to an exemplary embodiment of the present invention.

Alternatively, if, at Step 142, the medical information is determined by the data migration utility to correspond to a healthcare provider, then a duplicate healthcare provider dialog is opened at Step 150 and data migration paused. Referring to FIG. 16, the duplicate healthcare provider dialog may provide information about the pending healthcare provider, i.e., the healthcare provider in the source database. Similarly, the duplicate healthcare provider dialog may also provide information about the existing healthcare provider, i.e., the healthcare provider in the destination database. The duplicate healthcare provider dialog may then prompt the user to select the manner in which the healthcare provider information in the source database should be treated. For example, the user may select from: (1) adding the pending healthcare provider as a new healthcare provider in the destination database; (2) selecting another healthcare provider from the destination database to merge the pending healthcare provider's information with, merging the pending healthcare provider with the existing healthcare provider; or (3) skipping the pending healthcare provider, i.e., leaving the pending healthcare provider's information in the source database and not adding the same to the destination database.

Once the user has made the desired selection, the user may authorize the action, such as by selecting the OK button in FIG. 16. Once user authorization is provided, data migration is resumed in accordance with the user's previous selections. However, if the data migration utility determines at Step 152 in FIG. 5B that the user has indicated that another existing healthcare provider should be selected for merging with the pending healthcare provider, a select healthcare provider dialog is opened at Step 154 and the user to allowed to select a different existing healthcare provider from the destination database into which the pending healthcare provider information from the source database is merged.

Additionally, in one exemplary embodiment, the duplicate healthcare provider dialog may also include a button that allows the user to avoid the duplicate healthcare provider dialog for each duplicate healthcare provider identified. By selecting this option, each duplicate healthcare provider identified is added as a new healthcare provider in the destination database.

Further, if at any time during the migration of medical information, the data migration utility identifies a duplicate system definition, such as at Step 156, a duplicate system definition dialog is opened at Step 158 and data migration paused. The duplicate system definition dialog requires that the system definition in the source database is renamed before it can be migrated into the destination database. Once a new name is provided, the user may select an OK button in the duplicate system definition dialog to reinitiate data migration.

Figure 17:
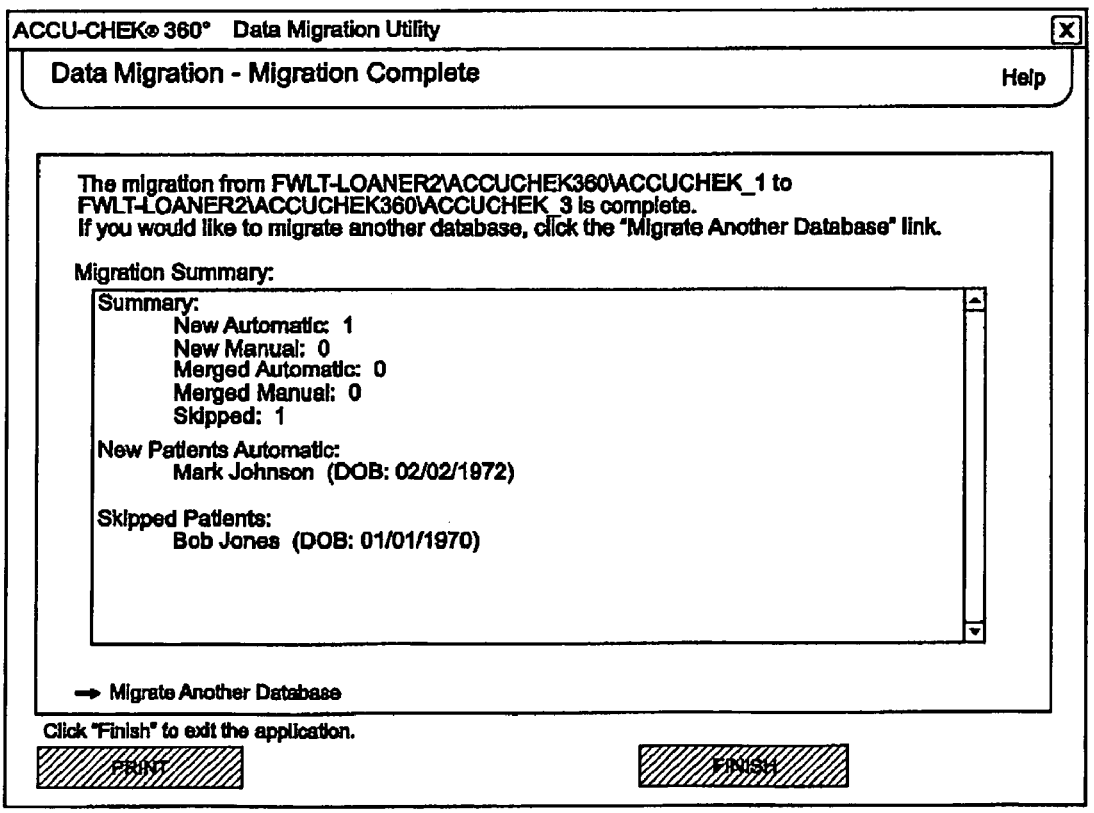
FIG. 17 is a screenshot of a data migration complete page according to an exemplary embodiment of the present invention.

Once the migration from the source database to the destination database of all data selected for migration is completed, the data migration utility opens the migration complete page at Step 160. As shown in FIG. 17, the migration complete page may include a listing of the medical information transferred that is separated into categories by patient and healthcare provider. Additionally, the patient category may be further separated by new patients, merged patients, and skipped patients. In one exemplary embodiment, the migration complete dialog also indicates the number of new patients created and/or patients merged automatically and manually. The migration complete page may also provided a detailed listing of patient names for each category, as well as some basic patient information, such as name, date of birth, and the patient's unique identification number. Additionally, in one exemplary embodiment, the data migration complete dialog provides similar information for each healthcare provider identified during the migration.

In order to migrate another database, the user may select the migrate another database option provided by the data migration complete dialog. If the migrate another database option is selected, the migration process is restarted, beginning at Step 104 in FIG. 5A. Alternatively, the data migration complete dialog may also include a close or finish button that may be selected by the user to close the data migration utility and end the same at End 162. Further, if at any time during operation of the data migration utility a user attempts to close the same, the data migration utility will close, any information transferred to the destination database is not saved, and the source database is restored.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A device for assisting in maintenance of medical records, comprising:
 a processor;
 a tangible computer readable memory;
 at least one patient database stored on the tangible computer readable memory and configured for storing a plurality of medical records, each of the plurality of medical records associated with a patient;
 a display; and
 a healthcare management software including a plurality of machine readable instructions executable by the processor, the healthcare management software configured to facilitate reading of at least one medical record stored in a medical device, each of the read medical records comprising medical data and medical device identification data, the healthcare management software further configured to associate the medical data of each read medical record with one of the patient databases by comparing the medical device identification data of the read medical record to an identification index, the identification index comprising an index indicating the medical device identification data assigned to each of the patient databases, the healthcare management software further configured to display the read medical records on the display to a user of the device, and the healthcare management software further configured to display a first user selectable option and a second user selectable option, activation of the first user selectable option causing assignment of the medical data of the medical record into the associated patient database, activation of the second user selectable option providing the user a first additional selectable option and a second additional selectable option, activation of the first additional selectable option permitting the user to select at least one read medical record for deletion and activation of the second additional selectable option permitting the user to select at least one read medical record for association with a different patient database.

2. The device of claim 1, wherein the healthcare management software is further configured to tag each of the read medical records as a new entry and to remove the new entry tag from the read medical record upon one of activation of the first user selectable option, deletion of the medical record, and association of the medical record with a different patient database.

3. The device of claim 1, wherein the medical device is adapted to generate the medical data of the medical record from a sample of the patient.

4. The device of claim 1, wherein the medical device identification data is one of a user generated identification key and the medical device serial number.

5. The device of claim 1, wherein activation of the second selectable option provides the user the further option to select all of the read medical records.

6. The device of claim 1, wherein the healthcare management software further includes instructions that when executed by the processor mark the selected read medical record as deleted and store the selected read medical record in a log file along with identification of the person making the selection.

7. The device of claim 1, wherein the second user selectable option is provided as an undo screen on the display, the undo screen including a listing of the read medical records and a selection tool for each of the read medical records.

8. The device of claim 7, wherein the undo screen includes a menu item, activation of which permits the user to remove from the database all medical records transferred during the last download of the medical device.

9. The device of claim 8, wherein activation of the menu item further generates a warning on the display before removing the medical records from the database, the warning indicating the date of the last download, information about the medical device, a total number of medical records, and a date range of the medical records.

10. The device of claim 1, wherein when the read medical record is selected and the second additional selectable option is activated, the healthcare management software causes the processor to prompt the user to identify a patient database with which to associate the selected read medical record.

11. A method of importing medical records from a portable device to a computer having a database of medical records relating to at least one patient, comprising the steps of:
 reading a plurality of medical records from a portable device, the step of reading performed by using a processor of the computer to execute a plurality of computer readable instructions of a healthcare management software stored on a tangible computer readable medium, each of the plurality of read medical records comprising medical data and portable device identification data;

associating each of the plurality of read medical records with a patient database stored on a memory of the computer, the step of associating performed by the healthcare management software comparing the portable device identification data of each of the plurality of downloaded medical records to an index reference stored on the memory of the computer, the index reference comprising an index indicating the portable device identification data assigned to each of the patient databases;

displaying with a display the plurality of medical records to a computer user before assigning the plurality of medical records with a patient database, the step of displaying with the display performed by the healthcare management software;

displaying with the display an user selectable undo download option to the user, the step of displaying with the display performed by the healthcare management software;

responding to activation of the user selectable undo download option by providing to the user with the display an additional user selectable option for the selection of at least one of the plurality of medical records for deletion and re-association to another patient database, the step of responding performed by the healthcare management software; and assigning the remaining medical records to the particular patient database the medical record was associated with in the step of associating, the step of assigning performed by the healthcare management software.

12. The method of claim 11, wherein the responding step includes allowing the user to select all of the plurality of medical records for one of deletion or re-association with the other patient databases.

13. The method of claim 11, wherein the responding step includes allowing the user to reassign the portable device identification data to another patient database.

14. The method of claim 11, wherein the reading step includes obtaining time data records from the portable device.

15. The method of claim 11, further including the step of tagging each of the plurality of downloaded medical records, the step of tagging performed by the healthcare management software and indicating the tagged medical record is newly read, wherein the tag is removed upon one of deletion of the medical record, re-association of the medical record to a another patient database, and inputting the medical record into the particular patient database.

16. The method of claim 11, wherein the medical data of the medical record is generated by the portable device from a patient sample.

17. The method of claim 11, wherein the step of reading comprises downloading the medical records from the medical device to a storage database on the computing device, the medical records removed from the storage database upon one of deletion of the medical record, re-association of the medical record to a another patient database, and inputting the medical record into the particular patient database.

18. The method of claim 11, wherein the portable device identification data of the medical record is one of a user generated portable device identification code and the portable device serial number.

19. A device for assisting in maintenance of medical records, comprising:
  a processor;
  a tangible computer readable memory;
  a first database stored on the tangible computer readable memory and configured for receiving a plurality of medical records, each of the plurality of medical records associated with a patient;
  at least one patient database stored on the tangible computer readable memory and configured for storing the plurality of medical records received by the first database;
  a display; and
  a healthcare management software including a plurality of machine readable instructions executable by the processor, the plurality of machine readable instructions configured to facilitate transfer of at least one medical record from a medical device to the first database, each of the transferred medical records comprising medical data and medical device identification data, the healthcare management software further configured to associate the medical data of each transferred medical record with one of the patient databases by comparing the medical device identification data of the transferred medical record to an identification index, the identification index comprising an index indicating the medical device identification data assigned to each of the patient databases, the healthcare management software further configured to display the transferred medical records on the display to a user of the device, and the healthcare management software further configured to display a first user selectable option and a second user selectable option, activation of the first user selectable option causing assignment of the medical data of the medical record into the associated patient database, activation of the second user selectable option providing the user a first additional selectable option and a second additional selectable option, activation of the first additional selectable option permitting the user to select at least one transferred medical record for deletion and activation of the second additional selectable option permitting the user to select at least one transferred medical record for association with a different patient database.

20. The device of claim 19, wherein the healthcare management software is further configured to tag each of the transferred medical records as a new entry, the healthcare management software configured to remove the new entry tag from the medical record upon one of activation of the first user selectable option, deletion of the medical record, and association of the medical record with a different patient database.

21. The device of claim 19, wherein when the second additional selectable option is activated and one of the transferred medical records is selected, the healthcare management software causes the processor to prompt the user to identify a patient database with which to associate the selected medical record.

22. A method of importing electronic medical data from a medical device to a computing device having a database configured to receive electronic medical data relating to at least one patient, the method comprising the steps of:
  generating at least one electronic medical data relating to a medical condition of a patient, the step of generating performed by a medical device, the medical device further assigning an electronic medical device identification key to the at least one electronic medical data;
  downloading the at least one electronic medical data and electronic medical device identification key assigned thereto onto a computing device having a processor, the step of downloading performed by a healthcare maintenance software comprising a plurality of computer readable instruction executable by the processor;
  associating a new download data tag with each of the at least one electronic medical data and electronic medical device identification key assigned thereto, the step of associating performed by the healthcare maintenance software;

inferring a patient database with which to input each of the at least one electronic medical data, the step of inferring performed by the healthcare maintenance software comparing the electronic medical device identification key assigned to the electronic medical data to an electronic identification reference index comprising an index indicating which of the electronic medical device identification key are assigned to specific patient databases, the patient databases stored on tangible a computer readable memory of the computing device; and presenting a user on a display a representation of the at least one electronic medical data, the representation presented indicating the inferred patient database for assigning the electronic medical records, the inferred patient database determined by the step of inferring, the step of presenting further including presenting the user a first user selectable option and a second user selectable option, wherein upon activation of the first user selectable option the electronic medical records are input into the inferred patient database and the new download data tag associated with the electronic medical record is removed, and upon activation of the second user selectable option the user is provided a first additional selectable option, a second additional selectable option, and a third additional selectable option, the first additional selectable option configured to allow the user to delete the electronic medical record from the computing device, the second additional selectable option configured to allow the user to assign a different patient database to the electronic medical record, the third additional selectable option configured to allow the user to assign the electronic medical device identification key to another patient.

23. The method of claim 22, wherein the step of downloading includes inputting the at least one electronic medical data and electronic medical device identification key assigned thereto into a storage database on one of the at least one tangible computer readable memory, the medical records removed from the storage database upon one of activation of the first user selectable option, deletion of the medical record, and association of the medical record to a different patient database.

24. The method of claim 22, wherein the medical device generates the electronic medical data from a sample of the patient.

* * * * *